US 8,278,311 B2

(12) United States Patent
Liu et al.

(10) Patent No.: US 8,278,311 B2
(45) Date of Patent: Oct. 2, 2012

(54) SUBSTITUTED PYRIMIDINE DERIVATIVES

(75) Inventors: Huaqing Liu, Buffalo Grove, IL (US); Irene Drizin, Wadsworth, IL (US); Marlon D. Cowart, Round Lake Beach, IL (US); Robert J. Altenbach, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 551 days.

(21) Appl. No.: 12/430,663

(22) Filed: Apr. 27, 2009

(65) Prior Publication Data
US 2009/0270364 A1    Oct. 29, 2009

Related U.S. Application Data

(60) Provisional application No. 61/048,331, filed on Apr. 28, 2008.

(51) Int. Cl.
*A61K 31/535* (2006.01)
*C07D 475/00* (2006.01)
(52) U.S. Cl. ..................... 514/257; 544/233
(58) Field of Classification Search .................. None
See application file for complete search history.

(56) References Cited

U.S. PATENT DOCUMENTS
2006/0035937 A1    2/2006 Wayne et al.

FOREIGN PATENT DOCUMENTS
WO    WO2008003702 A2    1/2008

OTHER PUBLICATIONS

Jantzen and Robinson. Modern Pharmaceutics, 1996, p. 596.*
Akdis et al., "Histamine receptors are hot in immunopharmacology", European Journal of Pharmacology, 2006, 533, 69-76.
Bell et al.,"Involvement of histamine H4 and H1 receptors in scratching induced by histamine receptor agonists in Balb C mice." British Journal of Pharmacology, 2004, 142, 374-380.
Bennett et al. "A peripheral mononeuropathy in rat that produces disorders of pain sensation like those seen in man", Pain, 1988, 33, 87-107.
Buckland et al., "Histamine induces cytoskeletal changes in human eosinophils via the H(4) receptor", British Journal of Pharmacology, 2003, 140, 1117-1127.
Caliskan et al., "Unusual manganese(III)-mediated oxidative free radical additions of 1,3-dicarbonyl compounds to benzonorbornadiene and 7-heterobenzonorbornadienes: mechanistic studies," J. Org. Chem, 2007, vol. 72, pp. 3353-3359.
Cianchi et al., "The role of cyclooxygenase-2 in mediating the effects of histamine on cell proliferation and vascular endothelial growth factor production in colorectal cancer," Clinical Cancer Research, 2005, 11 (19), 6807-6815.
Coge et al., "Structure and Expression of the Human Histamine H4-Receptor Gene", Biochemical and Biophysical Research Communications, 2001, 284, 301-309.

Collins et al., "Emerging therapies for neuropathic pain", Expert Opinion on Emerging Drugs, 2005, 10 (1), 95-108.
Coruzzi et al., Antiinflammatory and antinociceptive effects of the selective histamine H4-receptor antagonists JNJ7777120 and VUF6002 in a rat model of carrageenan-induced acute inflammation, European Journal of Pharmacology, 2007, 563, 240-244.
Coruzzi et al., "Gastric Effects of the Histamine H4 Receptor Antagonists JNJ7777120 and VUF6002" 35th Mtg of the European Histamine Research Society in Delphi, Greece (May 10-13, 2006) presentation O44.
de Esch I.J.P. et al., "The histamine H4 Receptor as a new therapeutic target for inflammation", Trends in Pharmacological Science, 2005, 26 (9), 462-469.
Dray et al., "Pharmacology of chronic pain", Trends in Pharmacological Sciences, 1994, 15 (6), 190-197.
Dunford et al.,"The histamine H4 receptor mediates allergic airway inflammation by regulating the activation of CD4+ T cells," The Journal of Immunology, 2006, 176, 7062-7070.
Dworkin R. et al., "An Overview of Neuropathic Pain: Syndromes, Symptoms, Signs, and Several Mechanisms", Clinical Journal of Pain, 2002, 18 (6), 343-349.
Eliel, E. L. et al., "Stereochemistry of Organic Compounds," 1994, pp. 119-120, 1206, John Wiley & Sons, Inc. New York.
Esbenshade et al., "Pharmacological and behavioral properties of A-349821, a selective and potent human histamine H3 receptor antagonist", Biochemical Pharmacology, 2004, 68, 933-945.
Fogel et al., "Influence of H3/H4 Receptor Antagonist Thioperamide on Regional Haemodynamics in Rats with Trinitrobenzene Sulfonic Acid-Induced Colitis" 35th Mtg of the European Histamine Research Society in Delphi, Greece (May 10-13, 2006), p. 32.
Grzybowska-Kowalczyk et al., "Human and clinical aspects of histamine: Distribution pattern of histamine H4 receptor in human synovial tissue from patients with rheumatoid arthritis", Inflammation Research, 2007, 56, Supplement 1, S59-S60.
Gutzmer et al.,"Histamine H4 receptor stimulation suppresses IL-12p70 production and mediates chemotaxis in human monocyte-derived dendritic cells.," Journal of Immunology, 2005, 174, 5224-5232.

(Continued)

*Primary Examiner* — Nobel Jarrell
(74) *Attorney, Agent, or Firm* — Nancy J. Gettel; Portia Chen

(57) ABSTRACT

The present application describes substituted pyrimidine compounds of formula (I)

(I)

wherein X, $A^1$, $R^1$, $R^2$, $R^3$, $R^4$, $R^5$, $R^6$, $R^7$, $R^8$, $R^9$, p, q, r, v, and w are defined in the specification, compositions comprising such compounds, methods for making the compounds, and methods of treating and preventing the progression of diseases, conditions and disorders using such compounds and compositions.

10 Claims, No Drawings

OTHER PUBLICATIONS

Hagiwara H., et al., "Domino Michael-O-alkylation reaction: one-pot synthesis of 2,4-diacylhydrofuran derivatives and its application to antitumor naphthofuran synthesis," J. Chem. Soc. Perkins Trans. 1, 2001, vol. 22, pp. 2946-2957.

Higuchi T., et al., "Pro-Drugs as Novel Drug Delivery Systems (ACS Symposium Series, 14)," American Chemical Society, 1975, Table of Contents.

Hintz S. et al., "Regio- and Stereoselective Cyclization Reactions of Unsaturated Silyl Enol Ethers by Photoinduced Electron Transfer—Mechanistic Aspects and Synthetic Approach," Eur. J. Org. Chem., 1998, pp. 1583-1596.

Honore et al., "Interleukin-1 alpha beta gene-deficient mice show reduced nociceptive sensitivity in models of inflammatory and neuropathic pain but not post-operative pain", Behavioural Brain Research, 2006, 167, 355-364.

Igaz et al., in Histamine: Biology and Medical Aspects, 2004, 89-96.

Ikawa, et al., "Histamine H4 receptor expression in human synovial cells obtained from patients suffering from rheumatoid arthritis,"Biol. Pharm. Bull., 2005, vol. 28 (10), pp. 2016-2018.

IUPAC Commission on Nomenclature of Organic Chemistry: Rules for the Nomenclature of Organic Chemistry Section E: Stereochemistry, Pure Appl Chem, 1976, 45, 11-30.

Jablonowska et al., "Distribution pattern of histamine H4 receptor in human synovial tissue from patients with rheumatoid arthritis" 35th Mtg of the European Histamine Research Society in Delphi, Greece (May 10-13, 2006), presentation 036.

Joshi et al., "Animal models of pain for drug discovery", Expert Opinion on Drug Discovery, 2006, 1, 323-334.

Kim S. H. et al., "An experimental model for peripheral neuropathy produced by segmental spinal nerve ligation in the rat," Pain, 1992, vol. 50 (3), pp. 355-363.

Krueger K.M. et al., "G Protein-Dependent Pharmacology of Histamine H.sub.3 Receptor ligands: Evidence for Heterogeneous Active State Receptor Conformations", Journal of Pharmacology and Experimental Therapeutics, 2005, 314 (1), 271-281.

Liu, et al., "Cloning and Pharmacological Characterization of a Fourth Histamine Receptor (H4) Expressed in Bone Marrow", Molecular Pharmacology, 2001, 59, 420-426.

Liu et al., "Comparison of Human, Mouse, Rat, and Guinea Pig Histamine H4 Receptors Reveals Substantial Pharmacological Species Variation", Journal of Pharmacology and Experimental Therapeutics, 2001, 299, 121-130.

Liu H., et al., "Cis-4-(piperazin-l-yl)-5,6,7a,8,9,10,11,11 Ia-octahydrobenzofuro [2, 3-h] quinazolin-2-amine(A-987306), A new histamine H4R antagonist that blocks pain responses against carrageenan-induced hyperalgesia", Journal of Medicinal Chemistry, 2008, 51 (22), 7094-7098.

Maslinska, et al., "Toll-like receptors (TLRs) and histamine receptor H4 in articular tissues of patients with rheumatoid arthritis (RA)" 34th Mtg of the European Histamine Research Society in Bled, Slovenia (May 11-15, 2005), Poster P-03.

Molander G. A. et al., Sequenced reactions with samarium(II) iodide. Sequential intramolecular Barbier cyclization/Grob fragmentation for the synthesis of medium-sized carbocycles, J. Org. Chem., 2001, 66 (13), 4511-4516.

Nguyen, et al., "Discovery of a Novel Member of the Histamine Receptor Family", Molecular Pharmacology, 2001, 59, 427-433.

Oda et al.,"Molecular cloning of monkey histamine H4 receptor.," Journal of the Pharmacological Society, 2005, 98, 319-322.

Parsons et al., "Histamine and its receptors", British Journal of Pharmacology, 2006, 147, S127-S135.

PCT International Search Report for application No. PCT/US2009/041848, Mailed on Jul. 20, 2009, 3 pages.

Porreca et al., "Antinociceptive Pharmacology of N-[[4-(4,5-Dihydro-1H-imidazol-2-yl)phenylmethyl]-242-[[(4- methoxy-2,6-dimethylphenyl)sulfonyl]methylaminojethoxyl-N-methylacetamide, Fumarate (LF22-0542), a Novel Nonpeptidic Bradykinin B1 Receptor Antagonist", Journal of Pharmacology and Experimental Therapeutics, 2006, 318, 195-205.

Smith et al., "Neuropathic Pain and the Electrophysiology and Pharmacology of Nerve Injury", Drug Develop. Research, 2001, 54 (3), 140-153.

Smith et al., Vogel's Textbook of Practical Organic Chemistry, 1989, Ed. 5, Longman Scientific & Technical.

Stark., "Recent advances in histamine H3/H4 receptor ligands," Expert Opinion in Therapeutic Patents, 2003, vol. 13 (6), pp. 851-865.

Thurmond et al., "A Potent and Selective Histamine H4 Receptor Antagonist with Anti-Inflammatory Properties", Journal of Pharmacology and Experimental Therapeutics, 2004, 309, 404-413.

U.S. Appl. No. 11/863,925, filed Sep. 28, 2007, inventor Marlon D. Cowart.

Varga et al.,"Inhibitory effects of histamine H4 receptor antagonists on experimental colitis in the rat.," European Journal of Pharmacology, 2005, 522, 130-138.

Vinik et al., "Diabetic neuropathies", Medical Clinics of North America, 2004, 88 (4), 947-999.

Vogel G., et al., Drug Discovery and Evaluation, 2nd edition, 2002, Springer-Verlag, New York, pp. 702-706.

Zhu, et al., "Cloning, Expression, and Pharmacological Characterization of a Novel Human Histamine Receptor", Molecular Pharmacology, 2001, 59, 434-441.

* cited by examiner

SUBSTITUTED PYRIMIDINE DERIVATIVES

CROSS-REFERENCE SECTION

This application claims priority to provisional application Ser. No. 61/048,331 filed Apr. 28, 2008, which is incorporated herein by reference.

TECHNICAL FIELD

The invention relates to a series of substituted pyrimidine compounds, compositions comprising such compounds, methods for making the compounds, and methods of treating conditions and disorders using such compounds and compositions.

DESCRIPTION OF RELATED TECHNOLOGY

Histamine modulates a number of physiological activities, acting through specific histamine receptors (reviewed in Parsons and Ganellin, British Journal of Pharmacology (2006) 147, S127-S135; Igaz and Hegyesi, in Histamine: Biology and Medical Aspects (2004), 89-96; Editor(s): A. Falus; Published S. Karger A G, Basel). Four histamine receptors have been identified as playing distinct physiological roles. These are the histamine $H_1$ receptor, the histamine $H_2$ receptor, the histamine $H_3$ receptor, and the histamine $H_4$ receptor. Compounds that modulate, or affect, the activity of these receptors may be used to treat diseases. For example, the well-known role of $H_1$ receptors in modulating allergic reaction has led to the clinical development of drugs that treat allergic rhinitis and other diseases by antagonizing the action of naturally-occurring, or endogenous, histamine in the body. Histamine $H_2$ receptor antagonists have been developed and proven clinically useful in treating diseases associated with excess stomach acidity. The histamine $H_3$ receptor is found predominantly on nerve terminals in the central nervous system (CNS) and the peripheral nervous system, i.e., periphery, and antagonists of this receptor have been documented in studies that benefit mammalian cognitive processes, improve wakefulness, suppress symptoms of allergic rhinitis, and suppress weight gain. The histamine $H_4$ receptor is the most recently identified histamine receptor and has been characterized as a distinct histamine receptor. The histamine $H_4$ receptor has been found in a number of mammalian tissues and has been determined to modulate a number of physiological processes, including immunological function.

By use of histamine $H_4$ ligands in animal disease models as well as in in vitro and ex vivo studies, the histamine $H_4$ receptor has been demonstrated to play an important role in various physiological and pathophysiological processes. Separately, in experiments with histamine $H_4$ deficient (knock out) animals and cells and tissues from such histamine $H_4$ deficient animals, the histamine $H_4$ receptor has been demonstrated to play an important role in various physiological and pathophysiological processes. Examples of diseases and disorders where histamine $H_4$ receptors have been found to play an important role include, for example, asthma, allergy, rheumatoid arthritis, and inflammation.

The activity of histamine $H_4$ receptors can be modified or regulated by the administration of histamine $H_4$ receptor ligands. The ligands can demonstrate antagonist, inverse agonist, or partial agonist activity.

Histamine $H_4$ ligands in different structural classes have been reviewed (Schwartz, Expert Opinion in Therapeutic Patents (2003) vol. 13, pp. 851-865). It would be beneficial to provide additional compounds demonstrating $H_4$ receptor-modulating activity that can be incorporated into pharmaceutical compositions useful for therapeutic methods.

SUMMARY OF THE INVENTION

The invention is directed to a series of substituted pyrimidine derivatives, particularly macrocyclic fused substituted pyrimidine derivatives, as well as compositions comprising and methods of using the same. Compounds of the invention have the formula (I):

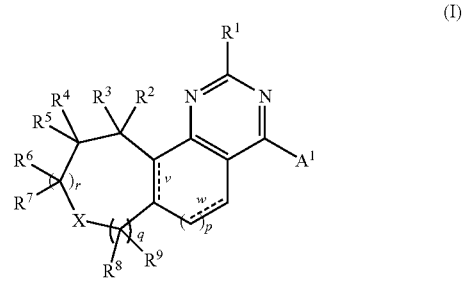

(I)

or a pharmaceutically acceptable, salt, ester, amide, or prodrug thereof, wherein v and w can be a single or double bond; with the proviso that w can be a single or a double bond when p is 1, and w can be only a single bond when p is 0 or 2;

$R^1$ is selected from hydrogen, —(C=O)—NH-alkylene (NR$^{13}$R$^{14}$), —(C=O)—(NR$^{13}$R$^{14}$), NH$_2$, —NH(acyl), —NH(alkyl), —N(alkyl)$_2$, —NH-alkylene-heteroaryl, —NH-alkylene(NR$^{13}$R$^{14}$), —NH(C=O)-alkylene (NR$^{13}$R$^{14}$), —NH(C=O)aryl, —NR$^{13}$(C=O)NR$^{13}$R$^{14}$, —NHOH, —NHOCH$_3$, —O-alkylene (NR$^{13}$R$^{14}$), alkoxy, alkoxycarbonyl, alkyl, carboxy, cyano, cyanoalkyl, cycloalkyl, fluoroalkyl, fluorocycloalkyl, hydroxyalkyl, and piperazine;

$R^2$, $R^3$, $R^4$, $R^5$, $R^6$, $R^7$, $R^8$ and $R^9$ are each independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, aryl, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, formyl, halogen, heteroaryl, heterocycle, hydrogen, hydroxy, hydroxyalkyl, mercapto, nitro, C(O)NR$^{13}$R$^{14}$, NR$^{11}$COalkyl, —NR$^{13}$R$^{14}$, —N(R$^{13}$)SO$_2$(R$^{14}$), —O-aryl, —O-heteroaryl, —S-aryl, and —SO$_2$(NR$^{13}$R$^{14}$);

$R^2$ and $R^4$ together with the atom they are attached may form a ring, alternatively, any two of $R^2$, $R^4$, $R^6$, and $R^8$, may optionally be taken together to form a bridge selected from —CH=CH—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;

$R^{11}$ is selected from alkoxyalkyl, alkyl, cyanoalkyl, cycloalkoxyalkyl, cycloalkyl, cycloalkylalkyl, fluoroalkyl, fluorocycloalkyl, fluorocycloalkylalkyl, hydrogen, and hydroxyalkyl;

$R^{12}$ is selected from the group consisting of alkoxyalkyl, fluoroalkyl, fluorocycloalkyl, fluorocycloalkylalkyl, and hydroxyalkyl;

$R^{13}$ and $R^{14}$ are each independently selected from acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluoroalkyl, fluorocycloalkyl, fluorocycloalkylalkyl, formyl, heteroaryl, heterocycle, hydrogen, hydroxy, and hydroxyalkyl;

$A^1$ is a group of structure $A^2$ or $A^3$ wherein A² is
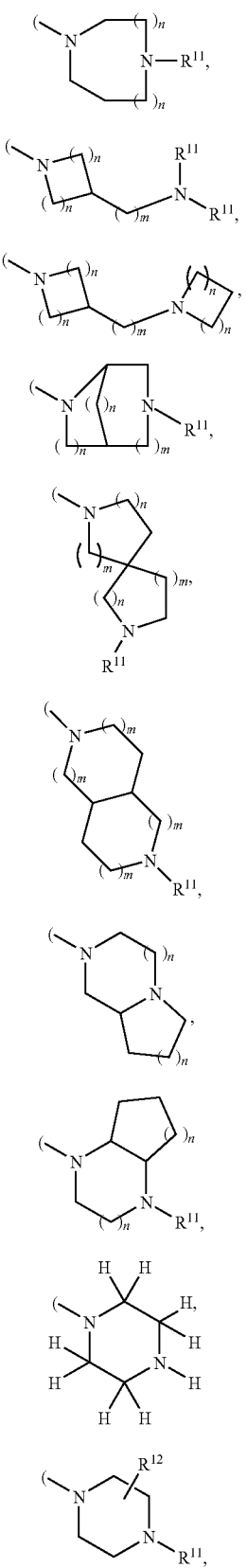
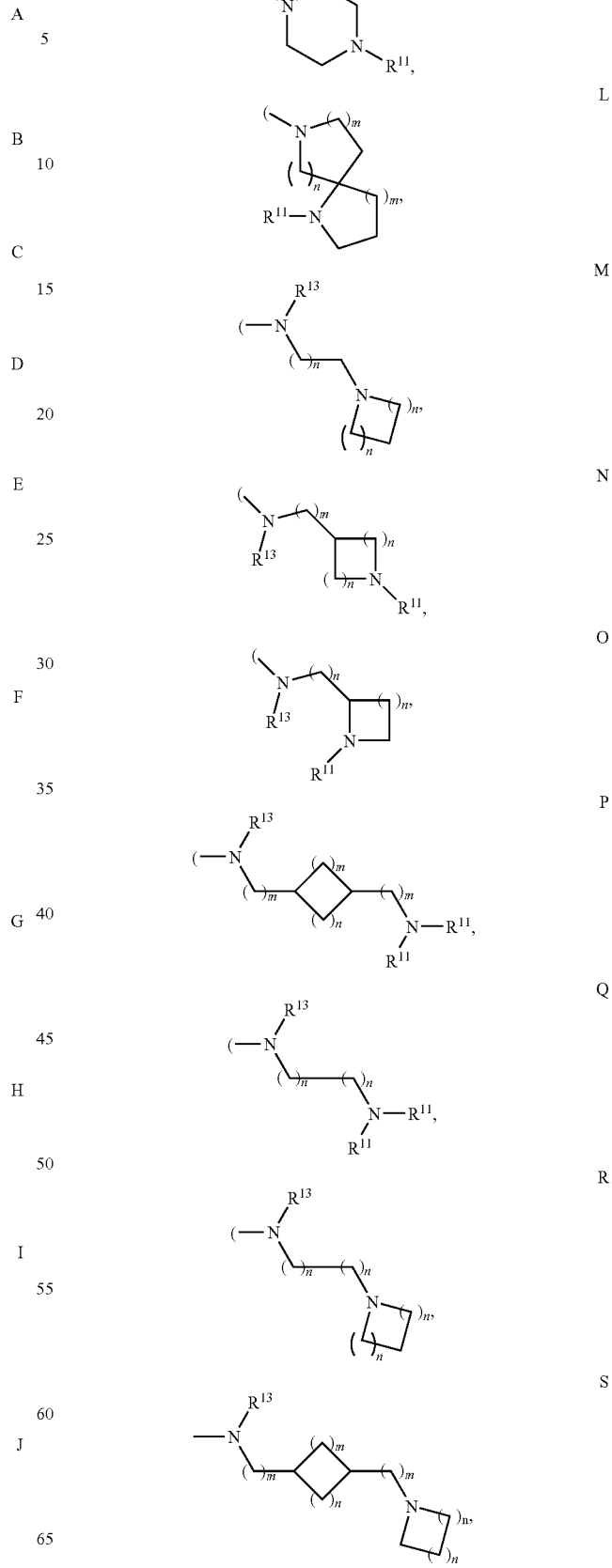

T
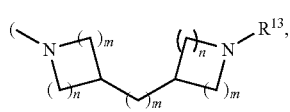
U
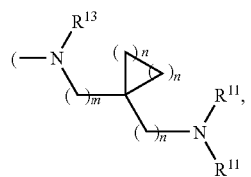
V
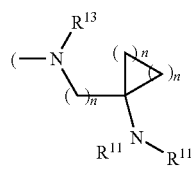
W
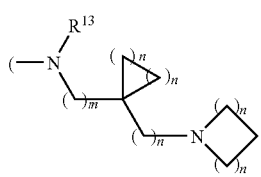
X
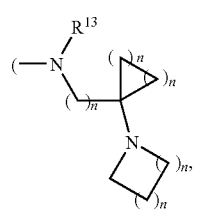
Y1
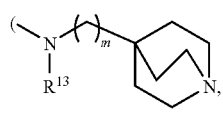
Y2
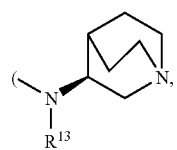
Y3
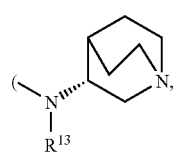
Y4
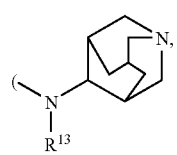
Y5
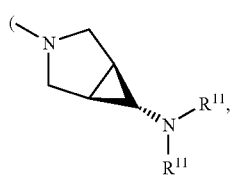
Y6
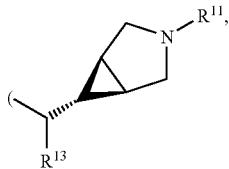
Y7
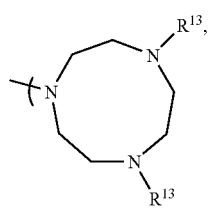
Y8
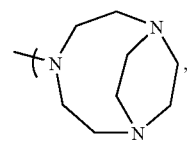
Y9
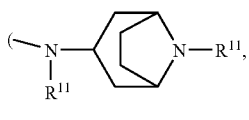
Y10
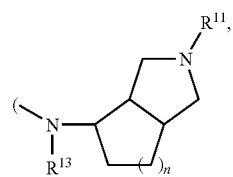
Y11
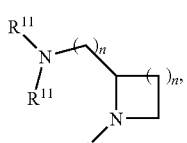
Y12
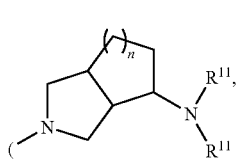
Y13
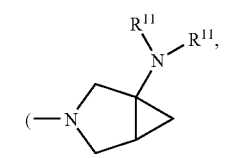
Y14
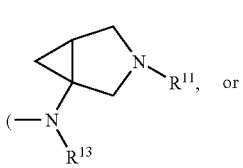
Y15

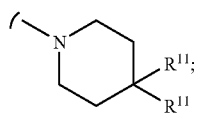

and A³ is selected from

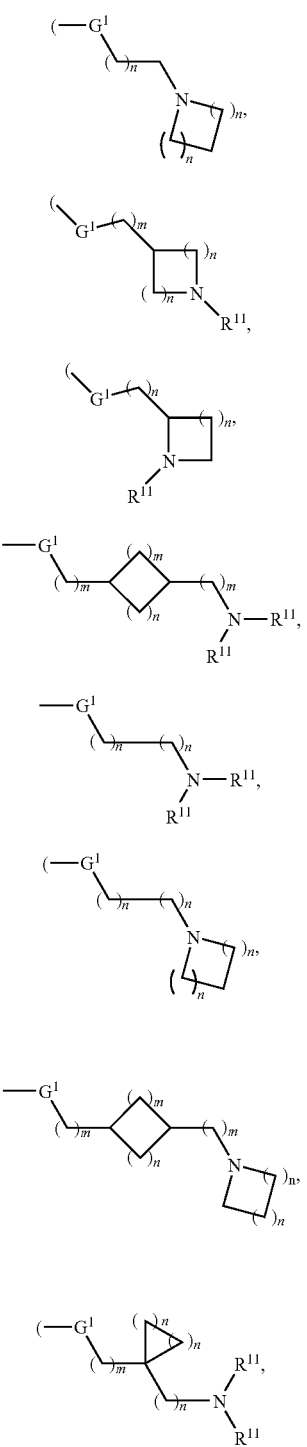

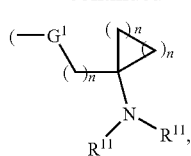
1V

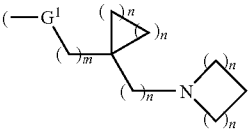
1W

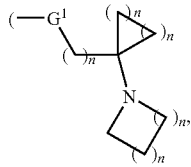
1X

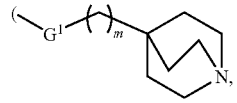
1Y1

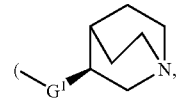
1Y2

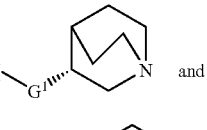
and 1Y3

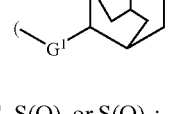
1Y4 wherein $G^1$ is O, S, S(O), or S(O)$_2$;
n is 1, 2, or 3;
m is 0, 1, or 2;
wherein each carbon atom of groups $A^1$ may be optionally substituted with one or more groups selected from acyl, acyloxy, alkenyl, alkoxy, alkoxyalkoxy, alkoxyalkyl, alkoxycarbonyl, alkyl alkylsulfonyl, alkylthio, alkynyl, amido, carboxy, cyano, cyanoalkyl, cycloalkoxyalkyl, cycloalkyl, cycloalkylalkyl, fluorine, fluoroalkoxy, fluoroalkyl, fluorocycloalkyl, fluorocycloalkylalkyl, formyl, hydroxy, hydroxyalkyl, mercapto, and nitro;
p is 0, 1, or 2;
q is 0 or 1;
r is 0 or 1; and
X is a bond, O, or S.

Another aspect of the invention relates to pharmaceutical compositions comprising compounds of the invention. Such compositions can be administered in accordance with a method of the invention, typically as part of a therapeutic regimen for treatment or prevention of conditions and disorders related to histamine H$_4$ receptor activity.

In addition, compounds of the invention can have the formula (I), and also demonstrate an ability to modulate histamine H$_4$ receptor activity. In this aspect, the invention relates to a method of modulating histamine H$_4$ receptor activity. The method is useful for treating, or preventing conditions and disorders related to histamine H$_4$ receptor modulation in mammals. More particularly, the method is useful for treating or preventing conditions and disorders related to the immune system involving inflammatory processes, auto-immune disease, and also in nervous system activities involved in pain, such as inflammatory pain, and non-inflammatory pain, especially neuropathic pain. Accordingly, the compounds and compositions of the invention are useful as a medication for treating or preventing histamine $H_4$ receptor modulated disease. Examples of such conditions and disorders include, but are not limited to, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, osteoarthritis pain, post-surgical pain, non-inflammatory pain, neuropathic pain, subcategories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

Another aspect of the invention relates to the use of the compounds of the invention, compounds of formula (I), in combination with histamine $H_1$ antagonists (such as loratidine), histamine $H_2$ antagonists (such as nizatidine), histamine $H_3$ antagonists (such as ABT-239), modulators of TNF-α (such as adalimumab), anti-inflammatory corticocosteroids (such as dexamethasone), 5-lipoxygenase inhibitors (such as zileuton), leukotriene antagonists (such as zafirlukast) or LTB4 antagonists, with NSAIDS (such as ibuprofen) including, COX-2 inhibitors (such as celecoxib), with β-adrenergic receptor agonists such as salmeterol, anti-nociceptive opiate agonists (such as morphine), anti-nociceptive alpha adrenergic agonists (such as dexmedetomidine), TRPV1 antagonists, nicotinic agonists such as ABT-418 or (1S,5S)-3-(5,6-dichloro-3-pyridinyl)-3,6-diazabicyclo[3.2.0]heptane, CB-1 agonists, CB-2 agonists, P2X7 antagonists, metabotropic glutamate receptor antagonists, an anti-convulsant such as gabapentin or pregabilin, and a tricyclic antidepressant such as amitriptyline.

The compounds, compositions comprising the compounds, and methods for treating or preventing conditions and disorders by administering the compounds, are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene," denotes a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, —CH=C(CH$_3$)CH$_2$—, and the like.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through a —C(=NH)— group, which also is defined as an imino group. Representative examples of alkoxyimino include, but are not limited to, (methoxy)imino, (ethoxy)imino and (tert-butoxy)imino.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, cycloalkyl, fluoroalkoxy, fluoroalkyl, formyl, halogen, hydroxy, hydroxyalkyl, mercapto, nitro, alkylthio, —NR$^{13}$R$^{14}$, (NR$^{13}$R$^{14}$)carbonyl, —SO$_2$NR$^{13}$R$^{14}$, and N(R$^{13}$)SO$_2$(R$^{14}$). Where the aryl group is a phenyl group, the number of substituents is 0, 1, 2, 3, 4, or 5. Where the aryl group is a bicyclic aryl, the number of substituents is 0, 1, 2, 3, 4, 5, 6, or 7. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —CO$_2$H group.

The term "cyano" as used herein means a —CN group, attached to the parent molecular moiety through the carbon.

The term "cyanoalkyl" as used herein means a —CN group attached to an alkylene, appended to the parent molecular moiety through the alkylene group. Representative examples of "cyanoalkyl" include, but are not limited to, 3-cyanopropyl, and 4-cyanobutyl.

The term "cycloalkyl" as used herein means a saturated cyclic hydrocarbon group containing from 3 to 10 carbons. Examples of cycloalkyl include cyclopropyl, cyclobutyl, cyclopentyl, cyclohexyl, cycloheptyl, and cyclooctyl. $C_3$-$C_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, fluoroalkoxy, formyl, haloalkoxy, haloalkyl, halogen, hydroxy, hydroxyalkyl, mercapto, oxo, nitro, alkylthio, —NR$^{13}$R$^{14}$, (NR$^{13}$R$^{14}$)carbonyl, —SO$_2$N(R$^{13}$)(R$^{14}$), and —N(R$^{13}$)SO$_2$(R$^{14}$), wherein, R$^{13}$ and R$^{14}$ are defined herein.

The term "cycloalkoxyalkyl" as used herein means a cycloalkyl group, as defined herein, appended to the parent molecular moiety through an —O-alkyl- group, wherein alkyl is as defined herein. Representative examples of cycloalkoxyalkyl include, but are not limited to, cyclobutoxymethyl, cyclopentyloxymethyl, 2-(cyclopentyloxy)ethyl and cyclohexyloxymethyl.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. ($C_3$-$C_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through an alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "fluorocycloalkyl" as used herein means a fluoro as defined herein, attached to a cycloalkyl moiety, attached to the parent molecular moiety through the cycloalkyl group. Representative examples of fluorocycloalkyl include, but are not limited to, 4-fluorocyclohexyl, 2,2-difluorocyclobutyl and the like.

The term "fluorocycloalkylalkyl" as used herein means a fluorocycloalkyl group as defined herein, attached to the parent molecular moiety through the alkyl group. Representative examples of fluorocycloalkylalkyl include, but are not limited to, (4-fluorocyclohexyl)methyl, (2,2-difluorocyclobutyl)methyl and the like.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, refers to an aromatic ring containing one or more heteroatoms independently selected from nitrogen, oxygen, and sulfur. Such rings can be monocyclic or bicyclic as further described herein.

The terms "monocyclic heteroaryl" or "5- or 6-membered heteroaryl ring", as used herein, refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contain 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and one oxygen atom. The 5- or 6-membered heteroaryl is connected to the parent molecular moiety through any carbon atom or any nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring wherein one or more of the atoms of the ring has been replaced with at least one heteroatom selected from oxygen, sulfur, and nitrogen. The bicyclic heteroaryl of the invention may be attached to the parent molecular moiety through any available carbon atom or nitrogen atom contained within the heteroaryl ring. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —NR$^{13}$R$^{14}$, (NR$^{13}$R$^{14}$)carbonyl, —SO$_2$N(R$^{13}$)(R$^{14}$), and —N(R$^{13}$)SO$_2$(R$^{14}$). Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring may contain zero, one, or two double bonds provided that the ring, when taken together with a substituent, does not tautomerize with a substituent to form an aromatic ring. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4- benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR^{13}R^{14}$, ($NR^{13}R^{14}$)carbonyl, —$SO_2N(R^{13})(R^{14})$, and —$N(R^{13})SO_2(R^{14})$.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyl triflate, or an alkylchloroformate, $CH_2I_2$, or a dihaloboronate ester, for example with methyl iodide, benzyl iodide, triethylsilyl triflate, acetyl chloride, benzyl chloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "($NR^{13}R^{14}$)" as used herein means both an $R^{13}$ and $R^{14}$ group, wherein $R^{13}$ and $R^{14}$ are each as defined for compounds of formula (I), are appended to the parent molecular moiety through a nitrogen atom. The "($NR^{13}R^{14}$)" is appended to the parent molecular moiety through the nitrogen.

The term "($NR^{13}R^{14}$)alkyl" as used herein means an —$NR^{13}R^{14}$ group, as defined herein, appended to the parent molecular moiety through an alkylene group, as defined herein. Representative examples of ($NR^{13}R^{14}$)alkyl include, but are not limited to, 2-(methylamino)ethyl, 2-(dimethylamino)ethyl, 2-(amino)ethyl, 2-(ethylmethylamino)ethyl, and the like.

The term "($NR^{13}R^{14}$)carbonyl" as used herein means an —$NR^{13}R^{14}$ group, as defined herein, appended to the parent molecular moiety through a carbonyl group, as defined herein. Representative examples of ($NR^{13}R^{14}$)carbonyl include, but are not limited to, aminocarbonyl, (methylamino)carbonyl, (dimethylamino)carbonyl, (ethylmethylamino)carbonyl, and the like.

The term "($NR^{13}R^{14}$)sulfonyl" as used herein means a —$NR^{13}R^{14}$ group, as defined herein, appended to the parent molecular moiety through a sulfonyl group, as defined herein. Representative examples of ($NR^{13}R^{14}$)sulfonyl include, but are not limited to, aminosulfonyl, (methylamino)sulfonyl, (dimethylamino)sulfonyl and (ethylmethylamino)sulfonyl.

The term "—$N(R^{13})SO_2(R^{14})$" as used herein means an amino group attached to the parent moiety to which is further appended with a $R^{13}$ group as defined herein, and a $SO_2$ group to which is appended an ($R^{14}$) group as defined herein. Representative examples of —$N(R^{13})SO_2(R^{14})$ include, but are not limited to, N-methylmethanesulfonamide.

The term "—$SO_2(NR^{13}R^{14})$" as used herein means a $NR^{13}R^{14}$ group attached to a $SO_2$ group, appended to the parent moiety through the sulfonyl group. Representative examples of —$SO_2(NR^{13}R^{14})$ include, but are not limited to, (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetyl chloride, benzoyl chloride, benzyl bromide, benzyloxycarbonyl chloride, formylfluoride, phenylsulfonyl chloride, pivaloyl chloride, (tert-butyl-O—C=O)$_2$O, trifluoroacetic anhydride, and triphenylmethyl chloride.

The term "oxo" as used herein means (=O).

The term "sulfonyl" as used herein means a —$S(O)_2$— group.

Antagonists are ligands that block receptor activation by an agonist. In the case of the histamine $H_4$ receptor, a histamine $H_4$ receptor antagonist blocks activation of the histamine $H_4$ receptor by a histamine $H_4$ receptor agonist such as the endogenous agonist ligand histamine. Inverse agonists are ligands that block receptor activation more generally: they block intrinsic activation of a receptor that occurs in the absence of an agonist activation by an agonist, and also block receptor activation by an agonist. Partial agonists are ligands that bind to receptors but only partially activate the receptor; in so doing, partial agonists compete with full agonists and block full activation of the receptor. In the case of the histamine $H_4$ receptor, the endogenous agonist histamine is a full agonist.

Compounds of the Invention

Compounds of the invention can have the formula (I) as described in the Summary of the Invention. In addition, certain embodiments of the invention further describe compounds of formula (I):

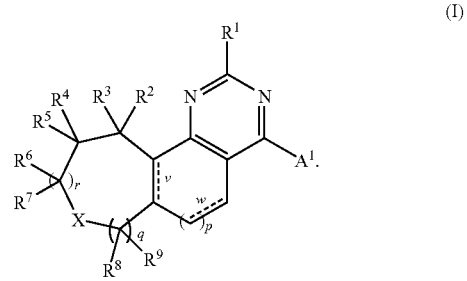

In a compound of formula (I), $R^1$ is hydrogen, —(C=O)—NH-alkylene($NR^{13}R^{14}$), —(C=O)—($NR^{13}R^{14}$), $NH_2$, —NH(acyl), —NH(alkyl), —N(alkyl)$_2$, —NH-alkylene-heteroaryl, —NH-alkylene($NR^{13}R^{14}$), —NH(C=O)-alkylene($NR^{13}R^{14}$), —NH(C=O)aryl, —$NR^{13}$(C=O)$NR^{13}R^{14}$, —NHOH, —NHOCH$_3$, —O-alkylene($NR^{13}R^{14}$), alkoxy, alkoxycarbonyl, alkyl, carboxy, cyano, cyanoalkyl, cycloalkyl, fluoroalkyl, fluorocycloalkyl, hydroxyalkyl, and piperazine. Preferably, $R^1$ is $NH_2$.

$R^2$, $R^3$, $R^4$, $R^5$, $R^6$, $R^7$, $R^8$ and $R^9$ are each independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, aryl, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, formyl, halogen, heteroaryl, heterocycle, hydrogen, hydroxy, hydroxyalkyl, mercapto, nitro, C(O)$NR^{13}R^{14}$, $NR^{11}$COalkyl, —$NR^{13}R^{14}$, —N($R^{13}$)SO$_2$($R^{14}$), —O-aryl, —O-heteroaryl, —S-aryl, and —SO$_2$($NR^{13}R^{14}$). Preferably, $R^2$, $R^3$, $R^4$, $R^5$, $R^6$, $R^7$, $R^8$ and $R^9$ are hydrogen.

Any two of $R^2$, $R^4$, $R^6$, and $R^8$, may optionally be taken together to form a divalent bridge adjoining the atoms to which they are attached selected from —CH=CH—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—. In one embodiment, $R^2$ and $R^4$ taken together are —CH$_2$CH$_2$CH$_2$CH$_2$— forming a fused cyclohexyl ring. In another embodiment, $R^2$ and $R^8$ taken together are —CH$_2$=CH— or —CH$_2$CH$_2$— forming an ethylene or ethano bridge, respectively.

$R^{11}$ is selected from alkoxyalkyl, alkyl, cyanoalkyl, cycloalkoxyalkyl, cycloalkyl, cycloalkylalkyl, fluoroalkyl, fluorocycloalkyl, fluorocycloalkylalkyl, hydrogen, and hydroxyalkyl. $R^{11}$ is preferentially hydrogen, alkyl or cycloalkyl.

$R^{12}$ is selected from the group consisting of alkoxyalkyl, fluoroalkyl, fluorocycloalkyl, fluorocycloalkylalkyl, and hydroxyalkyl. In a particular embodiment, $R^{12}$ is hydrogen.

$R^{13}$ and $R^{14}$ are each independently selected from acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluoroalkyl, fluorocycloalkyl, fluorocycloalkylalkyl, formyl, heteroaryl, heterocycle, hydrogen, hydroxy, and hydroxyalkyl.

$A^1$ is a group of structure $A^2$ or $A^3$
wherein $A^2$ is:

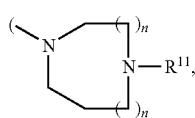

A

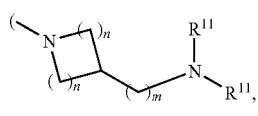

B

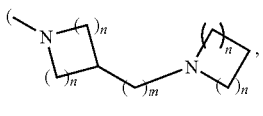

C

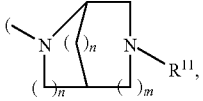

D

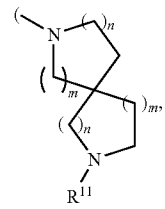

E

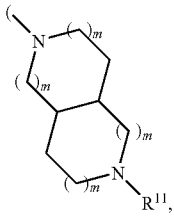

F

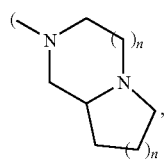

G

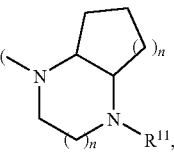

H

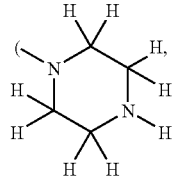

I

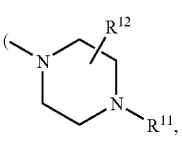

J

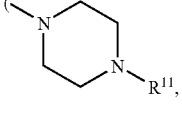

K

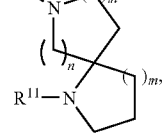

L

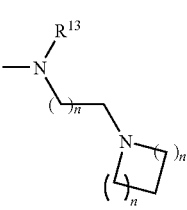

M

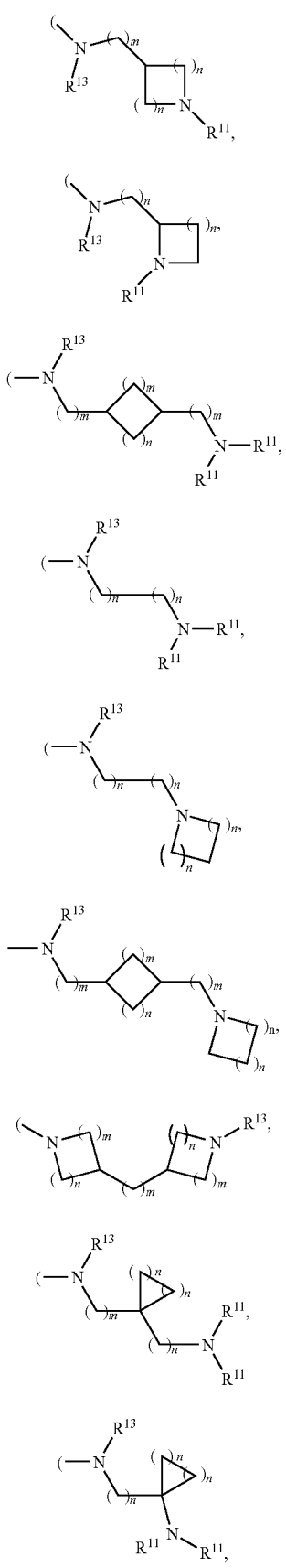
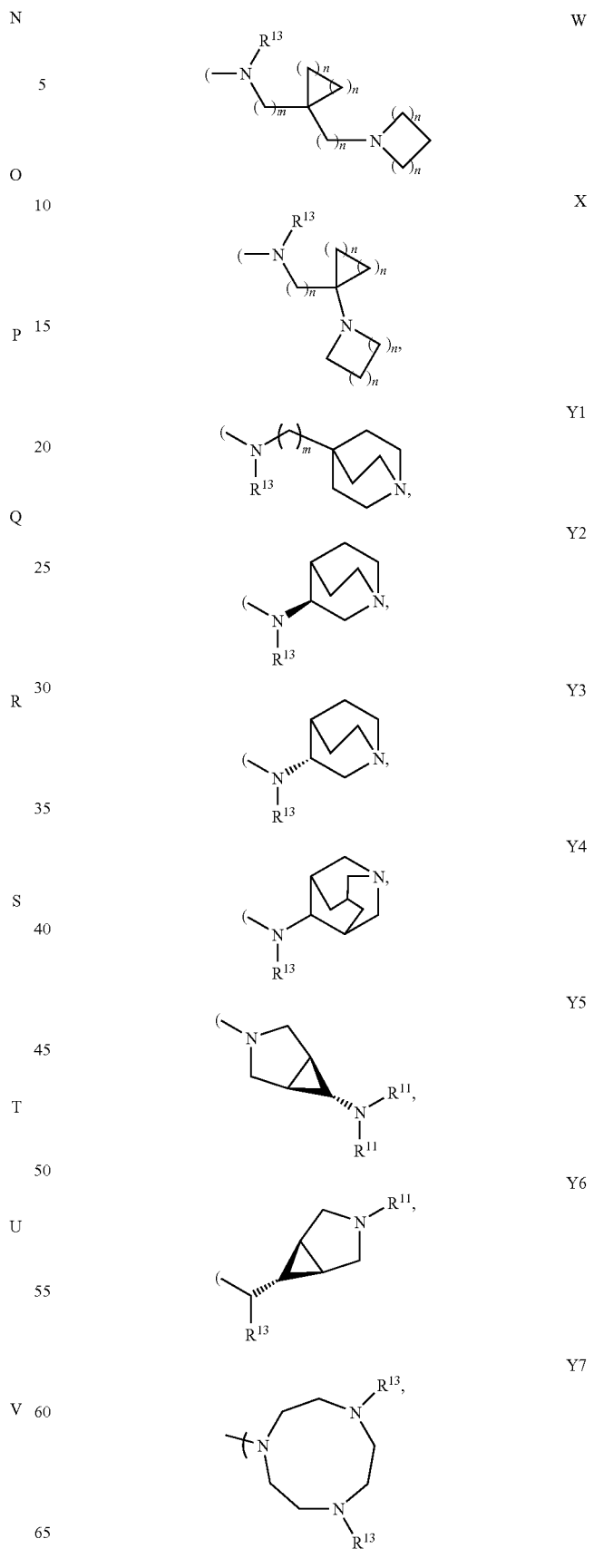

-continued
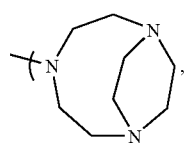 Y8
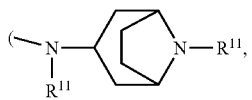 Y9
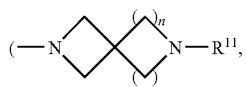 Y10
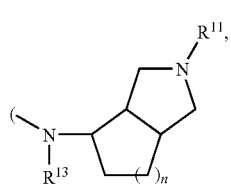 Y11
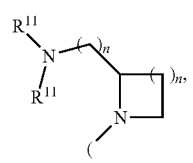 Y12
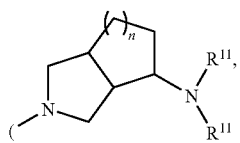 Y13
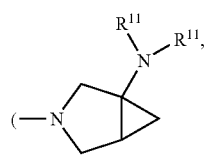 Y14
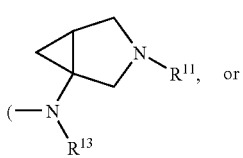 Y15, or
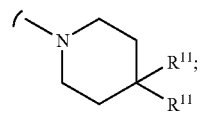 Y16;
and $A^3$ is selected from:
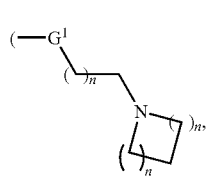 1M
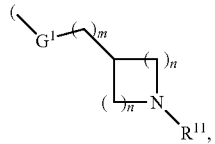 1N
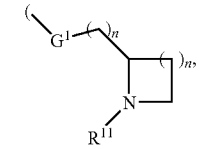 1O
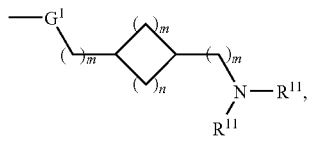 1P
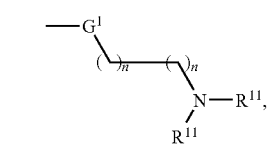 1Q
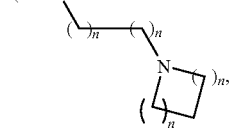 1R
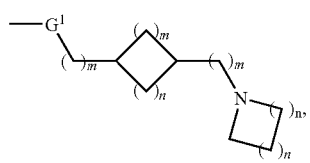 1S
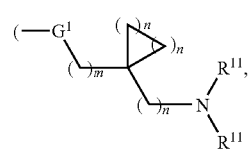 1U
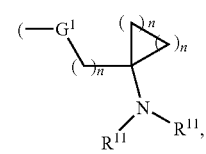 1V
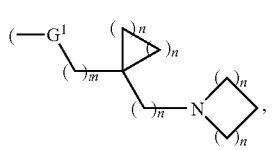 1W
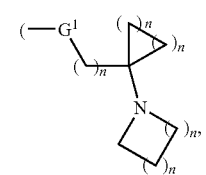 1X -continued

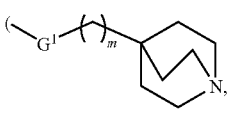
1Y1

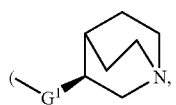
1Y2

 and
1Y3

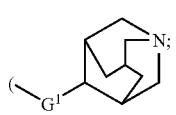
1Y4 wherein G¹ is O, S, S(O), or S(O)$_2$;
n is 1, 2, or 3;
m is 0, 1, or 2;
wherein each carbon atom of groups A¹ may be optionally substituted with one or more groups selected from acyl, acyloxy, alkenyl, alkoxy, alkoxyalkoxy, alkoxyalkyl, alkoxycarbonyl, alkyl alkylsulfonyl, alkylthio, alkynyl, amido, carboxy, cyano, cyanoalkyl, cycloalkoxyalkyl, cycloalkyl, cycloalkylalkyl, fluorine, fluoroalkoxy, fluoroalkyl, fluorocycloalkyl, fluorocycloalkylalkyl, formyl, hydroxy, hydroxyalkyl, mercapto, and nitro.

Specific groups contemplated for A¹ have the structure:

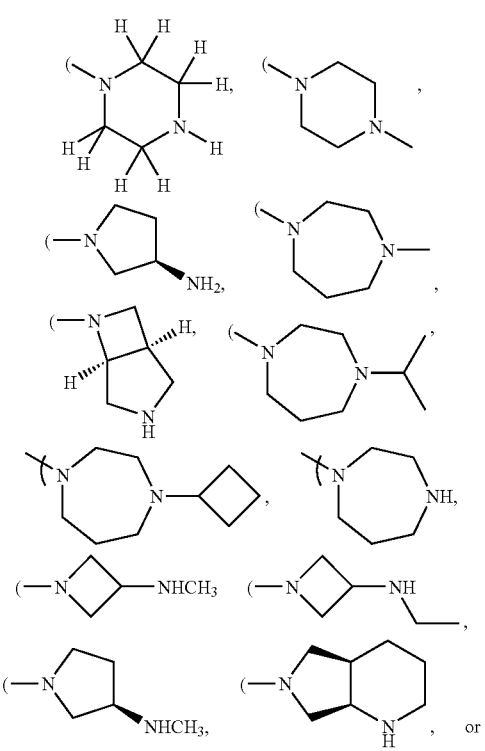

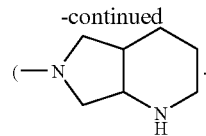

More particular and preferred structures for A¹ diamine groups of formulae (A)-(X) include, but are not limited to,

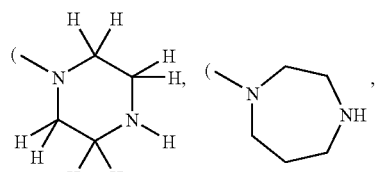

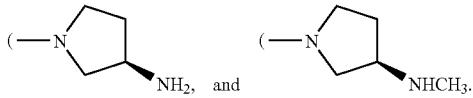

v and w can be a single or double bond; with the proviso that w can be a single or a double bond when p is 1, and w can be only a single bond when p is 0 or 2;
p is 0, 1, or 2.
r and q are independently 0 or 1.
X is a bond, O, or S.

In one embodiment, R¹ is NH$_2$, p is 1, v is a double bond, w is a single bond, R² and R⁴ joined together are —CH$_2$CH$_2$CH$_2$CH$_2$—, R³ and R⁵ are hydrogen, r and q are 0, and X is O.

In another embodiment, R¹ is NH$_2$, p is 1, v is a double bond, w is a double bond, R² and R⁴ joined together are —CH$_2$CH$_2$CH$_2$CH$_2$—, R³ and R⁵ are hydrogen, r and q are 0, and X is O.

In another embodiment, R¹ is NH$_2$; p is 1; v is a single bond; w is a single bond; R², R³, R⁴, R⁵, R⁶, R⁷, R⁸, and R⁹ are hydrogen; r and q are 1; and X is a bond.

In a further embodiment, R¹ is NH$_2$; p is 2; v is a single bond; w is a single bond; R² and R⁸ joined together are —CH═CH—; R³, R⁴, R⁵, R⁶, R⁷ and R⁹ are hydrogen; r and q are 1; and X is a bond.

In another embodiment, R¹ is NH$_2$; p is 2; v is a single bond; w is a single bond; R² and R⁸ joined together are —CH$_2$CH$_2$—; R³, R⁴, R⁵, R⁶, R⁷ and R⁹ are hydrogen; r and q are 1; and X is a bond.

Suitable groups for R², R³, R⁴, R⁵, R⁶, R⁷, R⁸ and R⁹ and A¹ in compounds of formula (I) are each independently selected. The described embodiments of the present invention may be combined. Such combination is contemplated and within the scope of the present invention. For example, it is contemplated that preferred groups for any of R², R³, R⁴, R⁵, R⁶, R⁷, R⁸ and R⁹ and A$_1$ can be combined with groups defined for any other of R², R³, R⁴, R⁵, R⁶, R⁷, R⁸ and R⁹ and A$_1$ whether or not such group is preferred.

There also exist a pharmaceutical composition comprising a compound of formula (I) and a pharmaceutically acceptable carrier.

Exemplary compounds of various embodiments of the invention include, but are not limited to:
4-piperazin-1-yl-5,6,7a,8,9,10,11,11a-octahydro[1]benzofuro[2,3-h]quinazolin-2-amine;
4-[(3R)-3-(methylamino)pyrrolidin-1-yl]-5,6,7a,8,9,10,11,11a-octahydro[1]benzofuro[2,3-h]quinazolin-2-amine;

(7aS,11aS)-4-piperazin-1-yl-5,6,7a,8,9,10,11,11a-octahydro[1]benzofuro[2,3-h]quinazolin-2-amine;
(7aR,11aR)-4-piperazin-1-yl-5,6,7a,8,9,10,11,11a-octahydro[1]benzofuro[2,3-h]quinazolin-2-amine;
4-(4-methyl-1,4-diazepan-1-yl)-5,6,7a,8,9,10,11,11a-octahydro[1]benzofuro[2,3-h]quinazolin-2-amine;
4-(4-methylpiperazin-1-yl)-5,6,7a,8,9,10,11,11a-octahydro[1]benzofuro[2,3-h]quinazolin-2-amine;
4-[(3R)-3-aminopyrrolidin-1-yl]-7a,8,9,10,11,11a-hexahydro[1]benzofuro[2,3-h]quinazolin-2-amine;
4-[(1R,5S)-3,6-diazabicyclo[3.2.0]hept-6-yl]-7a,8,9,10,11,11a-hexahydro[1]benzofuro[2,3-h]quinazolin-2-amine;
4-(1,4-diazepan-1-yl)-5,6,7a,8,9,10,11,11a-octahydro[1]benzofuro[2,3-h]quinazolin-2-amine;
4-(4-isopropyl-1,4-diazepan-1-yl)-5,6,7a,8,9,10,11,11a-octahydro[1]benzofuro[2,3-h]quinazolin-2-amine;
4-(4-cyclobutyl-1,4-diazepan-1-yl)-5,6,7a,8,9,10,11,11a-octahydro[1]benzofuro[2,3-h]quinazolin-2-amine;
trans-4-piperazin-1-yl-5,6,6a,7,8,9,10,10a-octahydrobenzo[h]quinazolin-2-amine;
cis-4-piperazin-1-yl-5,6,6a,7,8,9,10,10a-octahydrobenzo[h]quinazolin-2-amine;
trans-4-[3-(methylamino)azetidin-1-yl]-5,6,6a,7,8,9,10,10a-octahydrobenzo[h]quinazolin-2-amine;
trans-4-[3-(ethylamino)azetidin-1-yl]-5,6,6a,7,8,9,10,10a-octahydrobenzo[h]quinazolin-2-amine;
trans-4-[(3R)-3-(methylamino)pyrrolidin-1-yl]-5,6,6a,7,8,9,10,10a-octahydrobenzo[h]quinazolin-2-amine;
trans-4-[(3R)-3-aminopyrrolidin-1-yl]-5,6,6a,7,8,9,10,10a-octahydrobenzo[h]quinazolin-2-amine;
trans-4-octahydro-6H-pyrrolo[3,4-b]pyridin-6-yl-5,6,6a,7,8,9,10,10a-octahydrobenzo[h]quinazolin-2-amine;
cis-4-[(3R)-3-(methylamino)pyrrolidin-1-yl]-5,6,6a,7,8,9,10,10a-octahydrobenzo[h]quinazolin-2-amine;
cis-4-[(3R)-3-aminopyrrolidin-1-yl]-5,6,6a,7,8,9,10,10a-octahydrobenzo[h]quinazolin-2-amine;
cis-4-[cis-octahydro-6H-pyrrolo[3,4-b]pyridin-6-yl]-5,6,6a,7,8,9,10,10a-octahydrobenzo[h]quinazolin-2-amine;
cis-4-[3-(methylamino)azetidin-1-yl]-5,6,6a,7,8,9,10,10a-octahydrobenzo[h]quinazolin-2-amine;
cis-4-[3-(ethylamino)azetidin-1-yl]-5,6,6a,7,8,9,10,10a-octahydrobenzo[h]quinazolin-2-amine;
4-cis-octahydro-6H-pyrrolo[3,4-b]pyridin-6-yl-6,7,7a,8,11,11a-hexahydro-5H-8,11-ethanobenzo[6,7]cyclohepta[1,2-d]pyrimidin-2-amine;
4-[(3R)-3-(methylamino)pyrrolidin-1-yl]-6,7,7a,8,11,11a-hexahydro-5H-8,11-ethanobenzo[6,7]cyclohepta[1,2-d]pyrimidin-2-amine;
4-piperazin-1-yl-6,7,7a,8,11,11a-hexahydro-5H-8,11-ethanobenzo[6,7]cyclohepta[1,2-d]pyrimidin-2-amine;
4-cis-octahydro-6H-pyrrolo[3,4-b]pyridin-6-yl-6,7,7a,8,9,10,11,11a-octahydro-5H-8,11-ethanobenzo[6,7]cyclohepta[1,2-d]pyrimidin-2-amine; or
4-[(3R)-3-(methylamino)pyrrolidin-1-yl]-6,7,7a,8,9,10,11,11a-octahydro-5H-8,11-ethanobenzo[6,7]cyclohepta[1,2-d]pyrimidin-2-amine.

The practice of assigning names to chemical compounds from structures, and of assigning chemical structures from given chemical names is well known to those of ordinary skill in the art.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206. In a particular enantiomeric pair, the relative descriptors are reversed to indicate that this pair of enantiomers is of unknown absolute stereochemistry. For example, (−)-(7aS*,11aS*)-4-piperazin-1-yl-5,6,7a,8,9,10,11,11a-octahydro[1]benzofuro[2,3-h]quinazolin-2-amine and (+)-(7aR*,11aR*)-4-piperazin-1-yl-5,6,7a,8,9,10,11,11a-octahydro[1]benzofuro[2,3-h]quinazolin-2-amine are enantiomers of unknown absolute configuration.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes and cyclohexanes may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Methods of the Invention

Compounds and compositions of the invention are useful for modulating the histamine $H_4$ receptor, particularly by histamine $H_4$ receptor antagonism, partial agonism, or inverse agonism. In particular, the compounds and compositions of the invention can be used for treating and preventing disorders modulated by the histamine $H_4$ receptor. Typically, such disorders can be ameliorated by modulating histamine $H_4$ receptors in a mammal, preferably by administering a compound or composition of the invention, either alone or in combination with another active agent, for example, as part of a therapeutic regimen.

Certain substituted pyrimidine compounds, including but not limited to those specified as compounds of the invention, demonstrate the ability to affect histamine $H_4$ receptor activity, and in particular demonstrate histamine $H_4$ receptor antagonism. Such compounds can be useful for the treatment and prevention of a number of histamine $H_4$ receptor-mediated diseases or conditions. Compounds of the invention demonstrate such activity and have the formula (I), as previously defined herein.

There is also disclosed a method of treating a mammal having a condition where modulation of histamine $H_4$ receptor activity is of therapeutic benefit, said method comprising administering to a subject having or susceptible to said disorder with a therapeutically effective amount of a compound of the formula (I), or a pharmaceutically acceptable salt, ester, amide, or prodrug thereof, as presented in the Summary of the Invention and Detailed Description of the Invention sections herein.

There is also disclosed a method of treating a mammal having a condition where modulation of histamine $H_4$ receptor activity is of therapeutic benefit. The method comprises administering to a subject having or susceptible to said disorder a therapeutically effective amount of a compound of the formula (I), as previously defined.

The method is particularly beneficial when the condition or disorder is asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, or spinal cord injury pain.

In particular, it is particularly beneficial to administer compounds of formula (I) for the prevention and treatment of asthma.

It also is particularly beneficial to administer compounds of formula (I) for the prevention and treatment of inflammation.

It also is particularly beneficial to administer compounds of formula (I) for the prevention and treatment of pain. More particularly, it is beneficial to administer compounds of formula (I) for prevention and treatment of inflammatory pain. Compounds of formula (I) also demonstrate therapeutic benefit in treating and preventing non-inflammatory pain. In particular, compounds of formula (I) can be administered for treatment and prevention of neuropathic pain.

As an important consequence of the ability of the compounds of the invention to modulate the effects of histamine $H_4$ receptors in cells, the compounds described for the method of the invention can affect physiological processes in humans and animals. In this way, the compounds and compositions of formula (I) are useful for treating and preventing diseases and disorders modulated by histamine $H_4$ receptors. Typically, treatment or prevention of such diseases and disorders can be effected by modulating the histamine $H_4$ receptors in a mammal, by administering a compound or composition of the invention, either alone or in combination with another active agent as part of a therapeutic regimen.

Particularly preferred are compounds of formula (I) for the method, include, but are not limited to: 4-piperazin-1-yl-5,6,7a,8,9,10,11,11a-octahydro[1]benzofuro[2,3-h]quinazolin-2-amine; 4-[(3R)-3-(methylamino)pyrrolidin-1-yl]-5,6,7a,8,9,10,11,11a-octahydro[1]benzofuro[2,3-h]quinazolin-2-amine; (7aS,11aS)-4-piperazin-1-yl-5,6,7a,8,9,10,11,11a-octahydro[1]benzofuro[2,3-h]quinazolin-2-amine; (7aR,11aR)-4-piperazin-1-yl-5,6,7a,8,9,10,11,11a-octahydro[1]benzofuro[2,3-h]quinazolin-2-amine; and 4-(4-methyl-1,4-diazepan-1-yl)-5,6,7a,8,9,10,11,11a-octahydro[1]benzofuro[2,3-h]quinazol-2-amine.

Compounds of formula (I) can be administered to a subject having such a disorder or susceptible to such disorders in a therapeutically effective amount. The compounds are particularly useful for a method of treating a mammal having a condition where modulation of histamine $H_4$ receptor activity is of therapeutic benefit, wherein the method is accomplished by administering a therapeutically effective amount of a compound of formula (I) to a subject having, or susceptible to, such a disorder.

Compounds useful for the method of the invention include but are not limited to those specified in the examples and possess an affinity for the histamine $H_4$ receptor. Such compounds therefore may be useful for the treatment and prevention of diseases or conditions related to histamine $H_4$ modulation. Examples of such diseases or conditions are, for example, asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain. The ability of histamine $H_4$ receptor modulators, and consequently the compounds of the invention, to prevent or treat such disorders is demonstrated by evidence and examples found in references which follow.

Histamine $H_4$ receptor ligands have utility in treatment of a number of diseases and conditions, including asthma, allergy, allergic dermatitis, rheumatoid arthritis, inflammation, inflammatory bowel disease, colitis, ulcerative colitis, Crohn's disease, psoriasis, psoriatic arthritis, osteoarthritis, eczema, hives, multiple sclerosis, auto-immune encephalomyelitis, auto-immune disease, scleroderma, lupus, dermatitis, atopic dermatitis, rhinitis, allergic rhinitis, chronic obstructive pulmonary disease, septic shock, acute respiratory distress syndrome, cancer, pruritis, itching, pain, inflammatory pain, hyperalgesia, inflammatory hyperalgesia, migraine, cancer pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

The histamine $H_4$ receptor, or gene message coding for the histamine $H_4$ receptor (detected as cDNA by reverse transcriptase polymerase chain amplification (RTPCR) of cellular messenger (mRNA)), has been detected in a number of cells and tissues critically affected in disease conditions. For example, the histamine $H_4$ receptor plays a critical role in inflammation, in autoimmune disorders such as rheumatoid arthritis, and in disorders of the immune system. For example, the histamine $H_4$ receptor has been detected in cells of the immune system and in organs of the immune system: neutrophils, eosinophils, basophils, dendritic cells, mast cells, bone marrow, thymus, spleen, brain. For examples, see Liu, et al. Molecular Pharmacology (2001) vol. 59 pp. 420-426; de Esch, et al. Trends in Pharmacological Sciences vol. 26 No. 9 pp. 462-469; Oda, et al. Journal of the Pharmacological Society (2005) vol. 98, pp. 319-322; Zhu, et al. Molecular Pharmacology, (2001), v. 59, pp. 434-441; Gutzmer, et al. Journal of Immunology (2005) vol. 174 pp. 5224-5232; Coge, et al., Biochemical and Biophysical Research Communications (2001) vol. 284, pp. 301-309.

Histamine $H_4$ receptor is found at high (compared to normal) levels in disease tissues in rheumatoid arthritis, see for example, Grzybowska-Kowalczyk, et al. Inflammation Research (2007), 56, Supplement 1, S1-S2; Maslinska, et al. 34$^{th}$ Meeting of the European Histamine Research Society in Bled, Slovenia 2005 poster number 3; Jablonowska, et al. 35$^{th}$ Meeting of the European Histamine Research Society in Delphi, Greece (May 10-13, 2006) presentation O36; and Ikawa, et al. Biol. Pharm. Bull. (2005) vol. 28(10) pp. 2016-2018.

The role of histamine $H_4$ receptors in allergy, asthma, and allergic airway inflammation is shown by the finding that transgenic mice without histamine $H_4$ receptors are resistant to the development of disease in an animal model of asthma. The observation that a selective synthetic $H_4$ ligand elicits the same benefit in the asthma model also supports the benefits of $H_4$ ligands in treatment of disease. For example, see Dunford, et al. The Journal of Immunology (2006) vol. 176, pp. 7062-7070.

General reviews and papers on the role of histamine receptor in disease include Akdis and Simons, European Journal of Pharmacology (2006) vol. 533 pp. 69-76; de Esch, et al. Trends in Pharmacological Sciences vol. 26 No. 9 pp. 462-469; Thurmond, et al. Journal of Pharmacology and Experimental Therapeutics (2004) vol. 309 pp. 404-413; Buckland, et al. British Journal of Pharmacology (2003) vol. 140, 1117-1127. The utility for histamine $H_4$ receptor ligands in cancer is supported by the finding that the $H_4$ receptor has been found expressed on mammary cell carcinoma tissues, as reported by Maslinska, et al. 34$^{th}$ Meeting of the European Histamine Research Society in Bled, Slovenia (May 11-15, 2005) presentation. Histamine $H_4$ receptor activation was found to exert a proliferative effect in cancer tissues, Cianchi, et al. Clinical Cancer Research (2005) vol. 11(19) pp. 6807-6815. In gastritis and gastric lesions, histamine $H_4$ ligands were found to reduce the lesions induced by administration of indomethacin in vivo: Coruzzi, et al. Jablonowska, et al. 35$^{th}$ Meeting of the European Histamine Research Society in Delphi, Greece (May 10-13, 2006) presentation O44. In colitis, histamine $H_4$ ligands were found to reduce the lesions induced by administration of trinitrobenzesulfonic acid in vivo: Varga, et al. European Journal of Pharmacology (2005) vol. 522 pp. 130-138; and Fogel, et al. 35$^{th}$ Meeting of the European Histamine Research Society in Delphi, Greece (May 10-13, 2006) presentation P32. In itch and pruritus, the benefit of histamine $H_4$ receptor ligands has been shown by Bell, et al. British Journal of Pharmacology (2004) vol. 142, pp. 374-380.

The invention also relates to a use of the compounds of the invention as histamine $H_4$ receptor ligands to treat pain, including distinctly different types of pain, including inflammatory pain, chemically induced pain, pain resulting from surgery, pain resulting from burns, pain resulting from osteoarthritis, non-inflammatory pain, and neuropathic pain. The usefulness of histamine $H_4$ receptor ligands in treating pain has been demonstrated (U.S. patent application Ser. No. 11/863,925; also Coruzzi, et al., *Eur. J. Pharmacol.* 2007, 563, 240-244).

Neuropathic pain is distinct from other types of pain (e.g. inflammatory pain) in that it can develop in response to previous or ongoing tissue, nerve injury, or diabetes, but it persists long after signs of the original injury or damage have disappeared. Neuropathic pain is associated with allodynia, hyperalgesia, or causalgia (Dworkin Clinical Journal of Pain (2002) vol. 18(6) pp. 343-9). Allodynia is the perception of pain following a stimulus that would not normally be painful. Hyperalgesia is an enhanced response to a mildly noxious stimulus. Causalgia is described as a chronic burning pain that shows persistence in the absence of obvious noxious stimuli.

Neuropathic pain is not well treated with current therapies and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell, Expert Opinion on Emerging Drugs (2005) vol. 10(1), pp. 95-108; Vinik and Mehrabyan, Medical Clinics of North America (2004), vol. 88(4), pp. 947-999; Dray, Urban, and Dickenson Trends in Pharmacological Sciences (1994) vol. 15(6) pp. 190-7; and Dworkin, Clinical Journal of Pain (2002) vol. 18(6) pp. 343-9.

Neuropathic pain is a description that encompasses more specific names of pain that are sub-categories of neuropathic pain (Dworkin, Clinical Journal of Pain (2002) vol. 18(6) pp. 343-9) including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central poststroke pain, multiple sclerosis pain, Parkinson disease pain, and spinal cord injury pain.

A number of animal models of neuropathic pain that can be used to assess the ability of the compounds of the invention to treat neuropathic pain exist and are further discussed inter alia. Compounds of the invention are effective in treatment of neuropathic pain. Compounds of the invention are also effective in treating other types of pain, non-inflammatory pain, post surgical pain, and inflammatory pain.

A general review of animal models of pain including other types of pain that are not inflammatory or not due to ongoing inflammation, including osteoarthritis pain, cancer pain, and visceral pain is found in Joshi and Honore, Expert Opinion in Drug Discovery (2004) 1, pp. 323-334. Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in a pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 5 to about 500 micromoles/kg of body weight. For purposes of oral administration, more preferable doses can be in the range of from about 30 to about 500 micromoles/kg body weight. If desired, the effective daily dose can be divided into multiple doses for purposes of administration; consequently, single dose compositions may contain such amounts or submultiples thereof to make up the daily dose.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: BINAP for 2,2'-bis(diphenylphosphino)-1,1'-binaphthyl; Boc for butyloxycarbonyl; DMF for N,N-dimethylformamide; DMSO for dimethyl sulfoxide; EDTA for ethylenediaminetetraacetic acid; EtOAc for ethyl acetate; HPLC for high pressure liquid chromatography; IPA for isopropyl alcohol; LDA for lithium diisopropylamide; MCPBA for 3-chloroperoxybenzoic acid; Me for methyl; MeOH for methanol; Ms for methanesulfonyl; OAc for acetoxy; Pd for palladium; tBu for tert-butyl; TEA for triethylamine; TFA for trifluoroacetic acid; tetrahydrofuran for tetrahydrofuran; Tf represents trifluoromethanesulfonyl; Tris for trishydroxymethylaminomethane; Ts for para-toluenesulfonyl; dba for dibenzylidine acetone, and rt for "room temperature" or ambient temperature suitably ranging 17-30° C. As identifiers of compounds available from descriptions reported in the literature or available commercially, CAS numbers may be used; CAS numbers are identifier numbers assigned to compounds by Chemical Abstracts Service of the American Chemical Society, and are well known to those of ordinary skill in the art.

The compounds of this invention can be prepared by a variety of synthetic procedures. Representative procedures are shown in, but are not limited to Schemes 1-11.

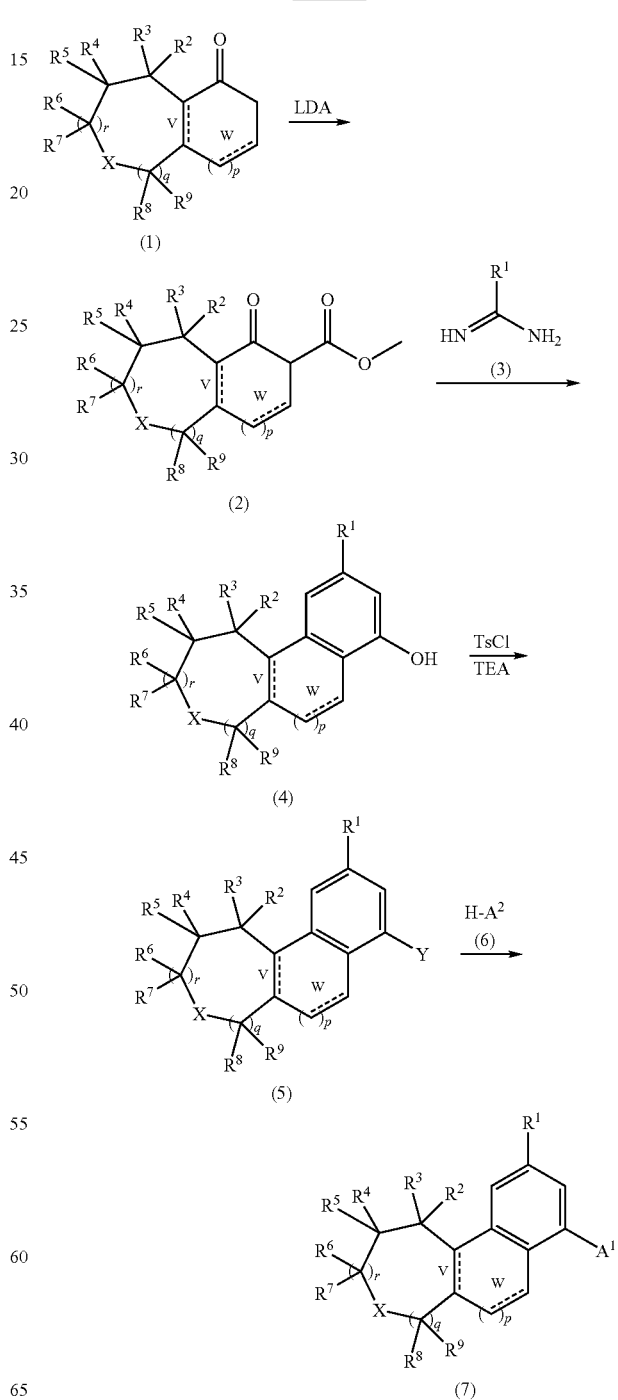

Compounds of formula (7), wherein $R^1$, $R^2$, $R^3$, $R^4$, $R^5$, $R^6$, $R^7$, $R^8$ and $R^9$, p, q, r, $A^1$, v, w and X are defined in formula (I), may be prepared as outlined in Scheme 1. Ketones of formula (1) which are obtained from commercial sources, or prepared by one who skilled in the art, when treated with a strong base such as but not limited to, lithium diisopropylamide, can be deprotonated and subsequently alkylated with either a carbonate such as dimethyl carbonate, or a chloroformate such as ethyl chloroformate to provide keto-esters of formula (2). Compounds of formula (2) when treated with a compound of formula (3), such as guanidine hydrochloride, optionally in the presence of a base such as potassium carbonate under heated conditions in a solvent such as N,N-dimethylformamide will provide compounds of formula (4). Compounds of formula (4) can exist as shown in the structure in Scheme 1 or in a tautomeric form. Compounds of formula (4) can be treated with reagents such as para-toluensulfonyl chloride, methylsulfonyl chloride or trifluoromethanesulfonyl chloride in the presence of a base such as triethylamine in a solvent such as pyridine or dichloromethane to provide compounds of formula (5) wherein Y is O—$SO_2$—R', wherein R' is alkyl, fluoroalkyl or aryl. Alternatively, compounds of formula (4) may also be treated with a chlorinating reagent such as but not limited to $POCl_3$, with or without heating as needed, to provide compounds of formula (5), wherein Y is Cl. Compounds of formula (5), wherein Y is —O—$SO_2$—R' or Y is Cl, when treated with compounds of formula (6), wherein (6) contains a primary or secondary nitrogen atom and H is a hydrogen atom on said nitrogen atom, under heated conditions in the presence or absence of a base such as triethylamine or diisopropylethylamine, in a solvent such as acetonitrile, ethanol, 2-methoxyethanol or toluene, will provide compounds of formula (7). Compounds of formula (7) are shown as racemates and can be separated using the techniques known to one skilled in the art such as chiral chromatography, fractional recrystallization or kinetic resolution to provide the corresponding enantiomers.

Compounds of formula (7) wherein $R^1$ is H, and $R^2$, $R^3$, $R^4$, $R^5$, $R^6$, $R^7$, $R^8$, $R^9$, p, q, r, $A^1$, v, w, and X are defined in formula (I) may be prepared by treating a compound of formula (2) with thiourea with heating in the presence of a base such as sodium methoxide in a solvent such as methanol, followed by reduction of the resulting product using a reagent such as Raney nickel to provide compounds of formula (4) wherein $R^1$ is H. Compounds of formula (4) wherein $R^1$ is H can be treated according to the method above to provide compounds of formula (7) wherein $R^1$ is H.

Compounds of formula (6) that contain two different nitrogen atoms may selectively react with compounds of formula (5) to provide one isomer of formula (7). Such selectivity may be the result of substitution or protecting groups attached to one of the nitrogen atoms. Alternatively, compounds of formula (6) that contain two different N—H groups may react with compounds of formula (5) in a non-selective manner wherein a mixture of two different compounds of formula (7) are obtained from the reaction. Mixtures of compounds of formula (7) are generally separated by methods known to one skilled in the art, such as silica based column chromatography, selective recrystallization, or both.

Scheme 2

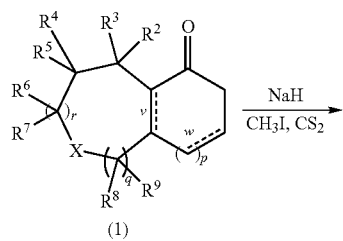

(1)

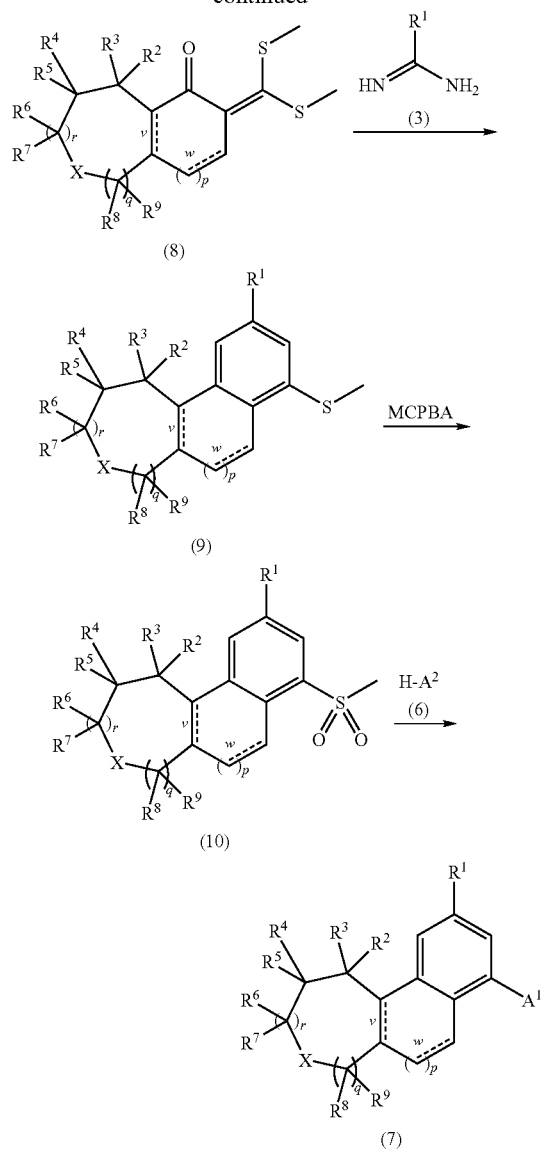

Alternatively, compounds of formula (7) wherein $R^1$, $R^2$, $R^3$, $R^4$, $R^5$, $R^6$, $R^7$, $R^8$, $R^9$, p q, r, $A^1$, v, w and X are defined in formula (I), may also be prepared as outlined in Scheme 2. Compounds of formula (1) prepared by one skilled in the art or obtained through commercial sources, when treated with carbon disulfide and iodomethane in the presence of a base such as but not limited to sodium hydride in a solvent such as but not limited to tetrahydrofuran will provide compounds of formula (8). Compounds of formula (8) when treated with a compound of formula (3), wherein $R^1$ is defined in formula (I), will provide sulfides of formula (9). Compounds of formula (9) when treated with an oxidizing agent such as MCPBA or Oxone® will provide sulfones of formula (10). Compounds of formula (10) when treated with compounds of formula (6), which contain a primary or secondary amine under heated conditions, in the presence or absence of a base such as triethylamine or diisopropyethylamine, in a solvent such as ethanol or 2-methoxyethanol, will provide compounds of formula (7), which is representative of present invention.

Scheme 3

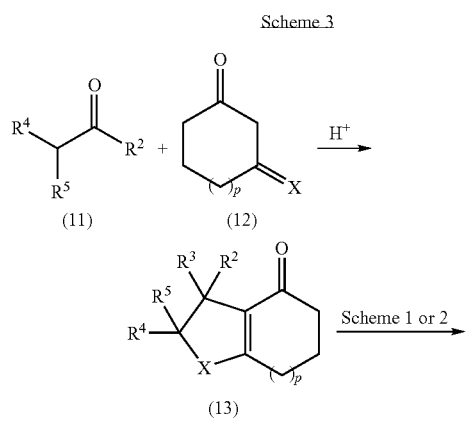

Scheme 4

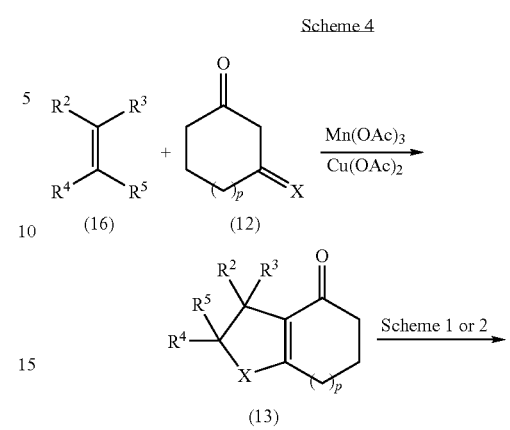

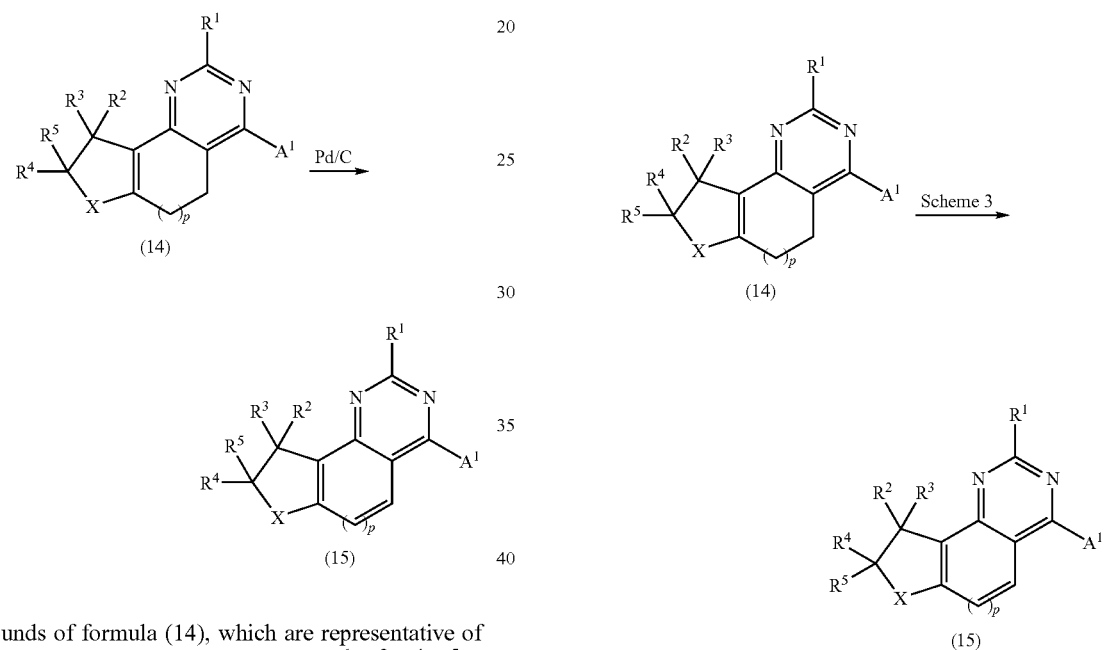

Compounds of formula (14), which are representative of compounds of the present invention wherein $R^1$, $R^2$, $R^4$, $R^5$, p and $A^1$ are defined in formula (I), wherein X is O or S, and $R^3$ is H, may be prepared as outlined in Scheme 3. Compounds of formula (11) and (12) obtained from commercial sources or prepared by one skilled in the art, when mixed and refluxed under a solvent with a high boiling point, such as but not limited to xylene, with a catalytic amount of an acid such as but not limited to toluenesulfonic acid to provide ketones of formula (13). Compounds of formula (13) can be converted to compounds of formula (14) according to the method described in Scheme 1 or 2. Compounds of formula (14) shown as racemates, can be separated using the techniques known to one skilled in the art such as chiral chromatography, fractional recrystallization or kinetic resolution to provide the corresponding enantiomers. Compounds of formula (14), wherein $R^1$, $R^2$, $R^4$, $R^5$ and $A^1$ are defined in formula (I), wherein X is O or S, $R^3$ is H, and p is 1, can be aromatized with an agent such as but not limited to palladium on carbon, trifluoroacetic acid, sulfur, selenium or 2,3-dichloro-5,6-dicyano-p-benzoquinone (DDQ) with or without heating in a solvent such as but not limited to methanol to provide compounds of formula (15), which are representative of compounds of the present invention.

Compounds of formula (14) which are representative of compounds of the present invention wherein $R^1$, $R^2$, $R^3$, $R^4$, $R^5$, p and $A^1$ are defined in formula (I), wherein X is O or S, may be prepared as outlined in Scheme 4. Compounds of formula (16), wherein $R^2$, $R^3$, $R^4$, and $R^5$ are defined in formula (1), obtained from commercial sources or prepared by one skilled in the art, when treated with compounds of formula (12) with a metal oxidant such as but not limited to manganese (III) triacetate and a co-oxidant such as but not limited to copper (II) acetate in a solvent such as but not limited to acetic acid will provide compounds of formula (13). References that describe this methodology may be found in the following: R. Caliskan et. al., J. Org. Chem. 72, 3353-3359 (2007), and the references cited in the article. Compounds of formula (13) can be converted to compounds of formula (14) according to the method described in Scheme 1 or 2. Compounds of formula (14) wherein $R^1$, $R^2$, $R^3$, $R^4$, $R^5$ and $A^1$ are defined in formula (I), wherein X is O or S, and p is 1, can be converted to compounds of formula (15) which are representative of compounds of present invention according to the method outlined in Scheme 3.

Scheme 5

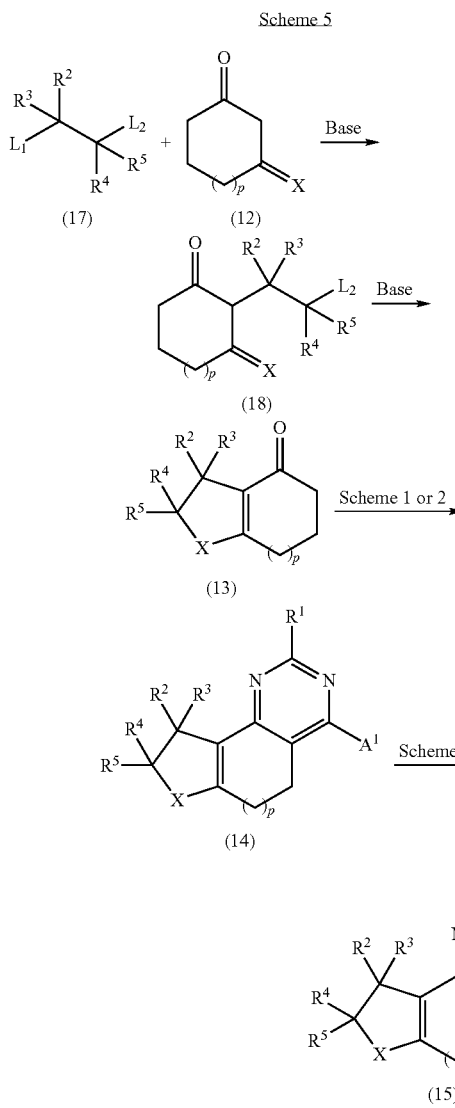

Scheme 6

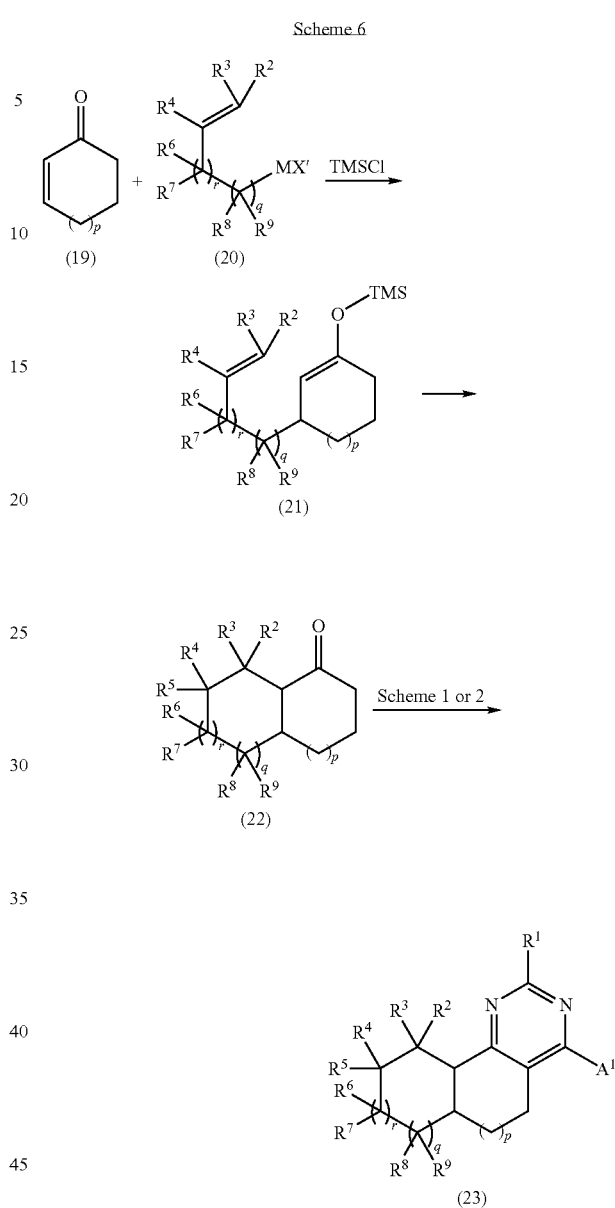

Additionally, compounds of formula (14) which are representative of compounds of the present invention wherein $R^1$, $R^2$, $R^3$, $R^4$, $R^5$, p and $A^1$ are defined in formula (I), wherein X is O or S, may be prepared as outlined in Scheme 5. Compounds of formula (17) wherein $L_1$ and $L_2$ represent two different or the same leaving groups such as halogen, or a group like O—$SO_2$—R', wherein R' is alkyl, fluoroalkyl or aryl, may be treated with compounds of formula (12) and a base such as but not limited to potassium carbonate in a solvent such as but not limited to acetonitrile to provide compounds of formula (18). The references of such a reaction can be found in: Molander, G. A. et. al., J. Org. Chem., (66)13, 4511-4516 (2001), and Hajiwara, H., et. al., J. Chem. Soc., Perkin 1, (22), 2946-2957, (2001). Compounds of formula (18) can be subsequently treated with or without a base to provide compounds of formula (13). Compounds of formula (13) can be transformed to compounds of formula (14) according to the method described in Scheme 1 or 2. Compounds of formula (14) wherein $R^1$, $R^2$, $R^3$, $R^4$, $R^5$ and $A^1$ are defined in formula (I), wherein X is O or S, and p is 1, can be converted compounds of formula (15) which are representative of compounds of present invention according to the method outlined in Scheme 3.

Compounds of formula (23) which are representative of compounds of the present invention wherein $R^1$, $R^2$, $R^3$, $R^4$, $R^6$, $R^7$, $R^8$, $R^9$, p, q, r and $A^1$ are defined in formula (I), wherein $R^5$ is H, may be prepared as outlined in Scheme 5. Compounds of formula (19), can be treated with compounds of formula (20) and a silane such as but not limited to chlorotrimethylsilane via a reaction well known as conjugate addition to provide silyl enol ethers of formula (21). Compounds of formula (20) are Grignard reagents, wherein MX' represents MgBr or MgCl that may be generated from the corresponding halide. The silyl enol ethers (21) can be cyclized under oxidative conditions via a process known as photoinduced electron transfer (PET) in a solvent such as but not limited to acetonitrile to provide compounds of formula (22). This methodology can be referenced from Hintz, S. et. al., Eur. J. Org. Chem., 1583-1596, (1998). Compounds of formula (22) can be transformed to compounds of formula (23) according to the method described in Scheme 1 or 2.

Scheme 7

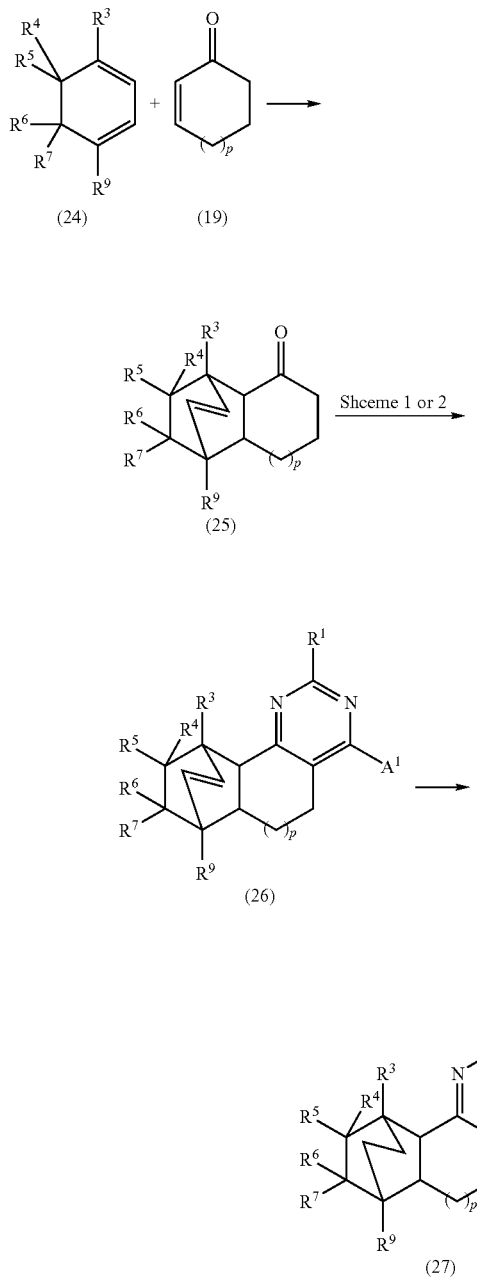

Scheme 8

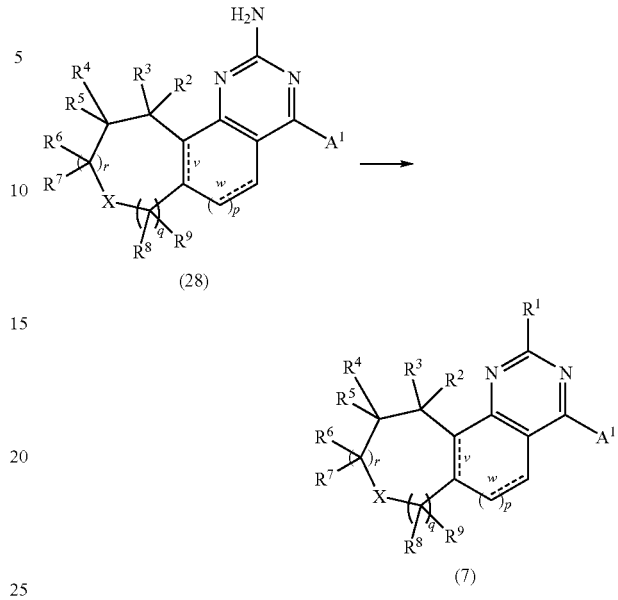

Compounds of formula (7), which are representative of compounds of the present invention wherein $R^2$, $R^3$, $R^4$, $R^5$, $R^6$, $R^7$, $R^8$, $R^9$, p, q, r, $A^1$, v, w and X are defined in formula (I), and wherein $R^1$ is limited to those compounds defined in formula (I) that are attached to the pyrimidine via a nitrogen atom may be prepared as outlined in Scheme 8. 2-Aminopyrimidines of formula (28) can be prepared as described in the Schemes herein. 2-Aminopyrimidines of formula (28) can be reacted with reagents such as (alkyl-CO)$_2$O, Y'-alkyl, alkylene-CO—Y', aryl-CO—Y', Y'-alkylene(NR$^{13}$R$^{14}$), Y'—(C=O)-alkylene(NR$^{13}$R$^{14}$) and Y'-alkylene-heteroaryl, wherein Y' is a leaving group such as Cl, Br, OMs, OTs or —O-succinimide optionally in the presence of a base such as Hunig's base or sodium hydride, pyridine or triethylamine, optionally in a solvent such as 2-methoxyethanol or N,N-dimethylformamide and optionally with heating to provide compounds of formula (7) wherein $R^2$, $R^3$, $R^4$, $R^5$, $R^6$, $R^7$, $R^8$, $R^9$, p, q, r, $A^1$, v, w and X are defined in formula (I) and $R^1$ is selected from —NH(acyl), —NH(alkyl), —N(alkyl)$_2$, —NH(C=O)aryl, —NH-alkylene(NR$^{13}$R$^{14}$), —NH(C=O)-alkylene(NR$^{13}$R$^{14}$), —NHOH, —NHOCH$_3$ and —NH-alkylene-heteroaryl.

Compounds of formula (26) and (27) which are representative of compounds of the present invention wherein $R^1$, $R^3$, $R^4$, $R^5$, $R^6$, $R^7$, $R^9$, p and $A^1$ are defined in formula (I), may be prepared as outlined in Scheme 7. Compounds of formula (19) and (24), obtained from commercial sources or prepared by one skilled in the art, can react via a well-known process such as a 4+2 cycloaddition reaction to provide the compounds of formula (25). Compounds of formula (25) can be converted to compounds of formula (26) according to the method described in Scheme 1 or 2. Compounds of formula (26) can be reduced with a catalyst such as but not limited to palladium on carbon under a hydrogen atmosphere to provide compounds of formula (27) which are representative of compounds of the present invention.

Scheme 9

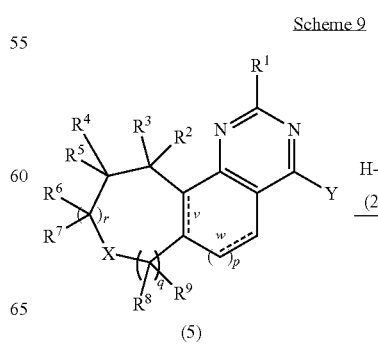

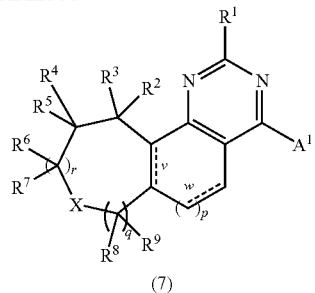

(7)

Additionally, compounds of formula (7), wherein $R^1$, $R^2$, $R^3$, $R^4$, $R^5$, $R^6$, $R^7$, $R^8$, $R^9$, p, q, r, $A^1$, v, w and X are defined in formula (I) may be prepared as outlined in Scheme 9. Alcohols and thiols of formula (29), and aminoalcohols and aminothiols wherein the nitrogen atom is protected with a protecting group such as a butoxycarbonyl group, which are obtained either from commercial sources or synthesized through the methods outlined herein, can be treated with a base such as sodium hydride, then treated with compounds of formula (5), wherein Y is Cl, p-toluenesulfonyl or $SO_2Me$, and then heated to provide compounds of formula (7). Alternative bases such as potassium tert-butoxide, potassium hydride, and potassium carbonate may also be employed. More generally, alcohols and thiols of formula (29) are described in the scientific literature and may be prepared by those or ordinary skill in the art of organic synthesis.

Compounds of formula (7), may be further reacted according to conditions known to those of ordinary skill in the art of organic synthesis to alter functional groups. For example, the removal of a protecting group such as Boc or hydrolysis of an ester group that will generate compounds of the present invention or be further transformed within the scope of other schemes described herein.

Scheme 10

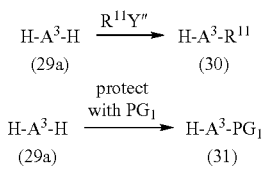

Compounds of formula (29a), wherein $A^3$ is defined in formula (I), are compounds wherein one of the H groups is a proton on an oxygen or sulfur atom and the other H group is a proton on a nitrogen atom of a primary or secondary amine. Compounds of formula (29a) can be directly reacted in Scheme 9 of the above in the presence of a strong base such as sodium hydride to provide compounds of formula (7). Alternatively, compounds of formula (29a) may be treated with an appropriate reagent such as $R^{11}$—Y''', wherein Y''' is a leaving group such as chlorine, bromine, iodine, mesylate or triflate, to provide compounds of formula (30) wherein the nitrogen atom of (30) is substituted with $R^{11}$. Alternatively, mono-protected diamines of formula (29a) may be treated with an appropriate aldehyde or ketone under condition of reductive amination to provide compounds of formula (30). Conditions commonly used for reductive amination include treatment of an amine (29a) with an aldehyde or ketone in the presence of $NaBH_3CN$ or $NaBH(OAc)_3$. Substituting compounds of formula (30) for compounds of formula (6) in the procedure outlined in Scheme 1 and 2 will provide compounds of formula (7) that are representative of the present invention. Compounds of formula (29a) may be treated with a reagent that will introduce a nitrogen-protecting group ($PG_1$) on the nitrogen atom of (29a). Some typical examples of common nitrogen protecting groups include but are not limited to tert-butoxycarbonyl or benzyloxycarbonyl, which are introduced by treating compounds of formula (29a) with 1 equivalent of an appropriate reagent such as di-tert-butyl dicarbonate or benzyl chloroformate, respectively, to provide compounds of formula (31) wherein the protecting group ($PG_1$) is connected to the nitrogen atom. Substituting compounds of formula (31) for compounds of formula (6) in the procedure outlined in Scheme 1 and 2 will provide compounds of formula (7), wherein the $A^1$ group of formula (7) contains a protected nitrogen atom. This said protected nitrogen atom of compounds of formula (7) can be deprotected using conditions known to one skilled in the art such as catalytic hydrogenation (e.g. in the presence of palladium on carbon in a solvent such as ethanol under an atmosphere of hydrogen) and acidic conditions (e.g. treatment with aqueous hydrochloric acid or with trifluoroacetic acid) to provide compounds of formula (7) that are representative of the present invention.

Scheme 11

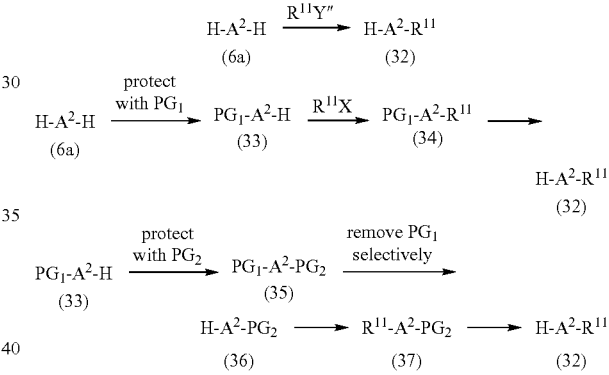

As outlined in Scheme 11, compounds of formula (6a) may contain two amine groups. The amine groups of compounds of formula (6a) may be either primary or secondary and can be used directly in the previous Schemes to provide compounds of present invention. Alternatively, compounds of formula (6a), which contain two N—H groups, may be treated with an appropriate reagent such as $R^{11}$—Y''', wherein X is a leaving group such as chlorine, bromine, iodine, mesylate or triflate, to provide compounds of formula (32) wherein one of the two N—H groups is substituted with $R^{11}$. Substituting compounds of formula (32) for compounds of formula (6) in the procedures outlined in the previous Schemes will provide compounds of formula (7) that are representative of the present invention.

Furthermore, compounds of formula (6a) that contain two amine groups may be treated with a reagent which will introduce a nitrogen protecting group ($PG_1$) on one of the amine groups. Some typical examples of common nitrogen protecting groups include but are not limited to benzyl, tert-butoxycarbonyl, benzyloxycarbonyl, or acetyl which are introduced by treating amines of formula (6a) with 1 equivalent of an appropriate reagent such as benzyl bromide, di-tert-butyl dicarbonate, benzyl chloroformate or acetic anhydride, respectively, to provide mono-protected diamines of formula (33). Mono-amine protected compounds of formula (33) can be further treated with an appropriate reagent such as $R^{11}$—Y'', wherein $R^{11}$ is defined in formula (I) and Y'' is a leaving group such as chlorine, bromine, iodine, mesylate or triflate, to provide compounds of formula (34). Compounds of formula (34) can be deprotected to provide compounds of formula (32), which can then be used to replace compounds of formula (6) in the procedures outlined in the previous Schemes to provide compounds of formula (7) which are representative of compounds of the present invention. Common conditions used for the deprotection of compounds of formula (34) to provide compounds of formula (32) include but are not limited to the following: catalytic hydrogenation (e.g. in the presence of palladium on carbon in a solvent such as ethanol under an atmosphere of hydrogen); acidic conditions (e.g. treatment with aqueous hydrochloric acid), or basic hydrolysis (e.g. treatment with aqueous sodium hydroxide and heat).

Alternatively, mono-protected diamines of formula (33) may be treated with an appropriate aldehyde or ketone under condition of reductive amination to provide diamines of formula (34). Conditions commonly used for reductive amination include treatment of an amine (33) with an aldehyde or ketone in the presence of $NaBH_3CN$ or $NaBH(OAc)_3$.

Mono-protected compounds of formula (33) can be treated with a second protecting group ($PG_2$) to provide di-protected compounds of formula (35). In di-protected compounds of formula (35), it is preferred that the choice of protecting groups is such that the protecting group $PG_1$ can be removed selectively without removing $PG_2$. Selective deprotection of $PG_1$ from compounds of formula (35) provide compounds of formula (36). Mono-protected compounds of formula (36) can be treated with an appropriate reagent such as $R^{11}$—Y'', wherein $R^{11}$ is as defined in formula (I) and X is a leaving group such as chlorine, bromine, iodine, mesylate or triflate, to provide compounds of formula (37). Alternatively, mono-protected compounds of formula (36) when treated with an appropriate aldehyde or ketone under condition of reductive amination will provide compounds of formula (37). Compounds of formula (37) can be deprotected to provide compounds of formula (32).

There are many groups of formula (6), (6a), (29) and (29a) that are available commercially or that can be prepared as described in the scientific literature of synthetic organic chemistry.

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral, intravenous, subcutaneous, intramuscular, intraperitoneal, intra-arterial, or intradermal injection, or for vaginal, nasal, topical, or rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals by oral administration, by injection, including by intravenous, subcutaneous, intramuscular, intraperitoneal, intra-arterial, and intradermal injection. The pharmaceutical compositions of this invention can be administered to humans and other mammals topically (as by powders, lotions, ointments or drops applied to the skin), bucally, or inhaled, as an oral or nasal spray. The pharmaceutical compositions of this invention can be administered to humans and other mammals intrarectally, or intravaginally. The term "parenterally," as used herein, refers to modes of administration which include intravenous, intramuscular, intraperitoneal, intrasternal, subcutaneous and intraarticular.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols(propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents that delay absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acids suitable for formation of addition salts by combination with the compounds of the invention include, but are not limited to, ascorbic acid, (D)-tartaric acid, (L)-tartaric acid, maleic acid, phosphoric acid, citric acid, hydrochloric acid, sulfuric acid and trifluoroacetic acid. Other acids include acetic, adipic, aspartic, glutamic, benzoic, benzenesulfonic, 4-methylbenzenesulfonic, camphorsulfonic, propionic, hydrobromic, glucuronic, methanesulfonic, ethanesulfonic, naphthylenesulfonic, lactic, fumaric, oxalic, and succinic acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound having a carboxylic acid moiety with an acid such as hydrochloric acid and an alcohol such as methanol, or ethanol.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl acid chloride. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

The compounds and processes of the invention will be better understood by reference to the following examples, which are intended as an illustration of and not a limitation upon the scope of the invention.

Unless otherwise described, reactions were carried out under ambient conditions (ranging 17-27° C.), under nitrogen. Unless otherwise described, column chromatography means flash chromatography carried out using silica gel, a technique well known to those of ordinary skill in the art of organic synthesis.

EXAMPLES

Example 1

4-piperazin-1-yl-5,6,7a,8,9,10,11,11a-octahydro[1]benzofuro[2,3-h]quinazolin-2-amine

Example 1A 3,4,5a,6,7,8,9,9a-octahydrodibenzo[b,d]furan-1(2H)-one

A solution of cyclohexanone (5.28 mL, 50.9 mmol), cyclohexane-1,3-dione (5.89 g, 50.9 mmol), and p-toluenesulfonic acid monohydrate (0.485 g, 2.55 mmol) in xylene (600 mL) was heated at reflux under a Dean Stark trap for 16 hours. The mixture was filtered and concentrated under reduced pressure. The residue was chromatographed on silica gel eluting with 0-30% ethyl acetate in hexanes to provide the title compound: $^1$H NMR (CDCl$_3$) δ 1.21-1.31 (m, 2H), 1.43-1.57 (m, 3H), 1.72-1.83 (m, 1H), 1.96-2.08 (m, 4H), 2.33 (t, 2H), 2.41 (t, 2H), 2.96-3.06 (m, 1H), 4.61-4.69 (m, 1H); MS (DCl/NH$_3$) m/z 193 (M+H)$^{30}$.

Example 1B methyl 1-oxo-1,2,3,4,5a,6,7,8,9,9a-decahydrodibenzo[b,d]furan-2-carboxylate A solution of diisopropylamine (5.56 mL, 39.0 mmol) in tetrahydrofuran (20 mL) was cooled to −78° C. and then treated with n-butyllithium (15.60 mL, 39.0 mmol) added dropwise. The mixture was stirred at this temperature for 30 minutes. The solution was transferred by cannula needle into a solution of the product from Example 1A, (3,4,5a,6,7,8,9,9a-octahydrodibenzo[b,d]furan-1(2H)-one, 2.5 g, 13.00 mmol) in tetrahydrofuran (40 mL) precooled to −78° C., and the resulting mixture was stirred for 30 minutes at −78° C. Then, dimethyl carbonate (11.71 g, 130 mmol) was added and the dry ice bath was removed. The mixture was stirred and allowed to warm to ambient temperature with stirring continued for 16 hours. The mixture was quenched with hydrochloric acid (1N, 40 mL) and diluted with ether (200 mL). The organic layer was separated and the aqueous layer was extracted with additional ether. The organic layers were combined and washed with brine, dried with anhydrous magnesium sulfate, and concentrated under reduced pressure. The residue was chromatographed on silica gel eluting with 10-30% ethyl acetate in hexanes to provide the title product: $^1$H NMR (CDCl$_3$) δ 1.23-1.30 (m, 1H), 1.42-1.56 (m, 3H), 1.72-1.84 (m, 1H), 1.87-2.04 (m, 3H), 2.17-2.26 (m, 1H), 2.31-2.49 (m, 3H), 2.56-2.67 (m, 1H), 3.00-3.10 (m, 1H), 3.32-3.40 (m, 1H), 3.75 (d, J=2.45 Hz, 2H), 4.67-4.75 (m, 1H); MS (DCl/NH$_3$) m/z 251 (M+H)$^+$.

Example 1C 2-amino-5,6,7a,8,9,10,11,11a-octahydro[1]benzofuro[2,3-h]quinazolin-4-ol A solution of the product from Example 1B (3.7 g, 14.78 mmol), guanidine hydrochloride (4.24 g, 44.3 mmol) and potassium carbonate (6.54 g, 47.3 mmol) in N,N-dimethylformamide (30 mL) was heated at 130° C. for 16 hours. After cooling to ambient temperature, the mixture was filtered through a layer of diatomaceous earth and washed with a small amount of N,N-dimethylformamide. The filtrate was concentrated under reduced pressure and the residue was azeotropically dried with toluene. The final residue was chromatographed on silica gel eluting with methanol:dichloromethane:ethyl acetate (5-10:45:45) to provide the title product: $^1$H NMR (DMSO-d$_6$) δ 1.13-1.27 (m, 2H), 1.35-1.55 (m, 3H), 1.66-1.81 (m, 1H), 1.87-2.00 (m, 2H), 2.31 (t, 2H), 2.57 (t, 2H), 2.82-2.93 (m, 1H), 4.58-4.66 (m, 1H), 6.14-6.24 (m, 2H); MS (DCl/NH$_3$) m/z 260 (M+H)$^+$.

Example 1D 2-amino-5,6,7a,8,9,10,11,11a-octahydro[1]benzofuro[2,3-h]quinazolin-4-yl4-methylbenzenesulfonate A solution of the product from Example 1C (570 mg, 2.198 mmol), p-toluenesulfonyl chloride (838 mg, 4.40 mmol) and 4-(dimethylamino)pyridine (53.7 mg, 0.440 mmol) in dichloromethane (40 mL) was treated with triethylamine (0.613 mL, 4.40 mmol) at ambient temperature and the resulting solution was stirred for 3 hours. It was diluted with dichloromethane (100 mL) and water, and partitioned. The organic layer was separated, dried with magnesium sulfate and concentrated under reduced pressure. The resulting residue was chromatographed on a silica gel column eluting with ethyl acetate:dichloromethane:hexane (20:40:40) to provide the title product: $^1$H NMR (CDCl$_3$) δ 1.20-1.34 (m, 2H), 1.48-1.60 (m, 3H), 1.72-1.84 (m, 1H), 2.00-2.13 (m, 2H), 2.43-2.49 (m, 5H), 2.79-2.89 (m, 2H), 2.99-3.10 (m, 1H), 4.64-4.73 (m, 3H), 7.35 (d, J=8.48 Hz, 2H), 7.94 (d, J=8.48 Hz, 2H); MS(DCl/NH$_3$) m/z 414 (M+H)$^+$.

Example 1E 4-piperazin-1-yl-5,6,7a,8,9,10,11,11a-octahydro[1]benzofuro[2,3-h]quinazolin-2-amine A solution of the product from Example 1D (535 mg, 1.29 mmol) and piperazine (334 mg, 3.88 mmol) in acetonitrile (10 mL) was treated with triethylamine (0.18 mL, 2.58 mmol), and heated to 90° C. for 16 hours. The mixture was cooled to ambient temperature and concentrated under reduced pressure. The resulting residue was chromatographed on silica gel column eluting with ammonium hydroxide/methanol/dichloromethane (0.8/8/92) to provide the title product: $^1$H NMR (CDCl$_3$) δ 1.23-1.33 (m, 2H), 1.46-1.59 (m, 3H), 1.72-1.86 (m, 1H), 2.06-2.18 (m, 2H), 2.42 (t, 2H), 2.69-2.79 (m, 2H), 2.92-3.00 (m, 4H), 3.00-3.09 (m, 1H), 3.09-3.15 (m, 4H), 4.52-4.60 (m, 2H), 4.62-4.69 (m, 1H); MS (DCl/NH$_3$) m/z 328 (M+H)$^+$.

Example 2

4-[(3R)-3-(methylamino)pyrrolidin-1-yl]-5,6,7a,8,9,10,11,11a-octahydro[1]benzofuro[2,3-h]quinazolin-2-amine

Example 2A tert-butyl (3R)-1-benzylpyrrolidin-3-yl(methyl)carbamate

To a solution of (3R)-(−)-1-benzyl-3-(methylamino)pyrrolidine (200 mg, 1.05 mmol) and di-tert-butyl-dicarbonate (230 mg, 1.06 mmol) in methanol (10 mL) was added sodium hydroxide (10%, 4 mL) and the mixture stirred at ambient temperature for 1 hour. The mixture was diluted with water (20 mL) and ethyl acetate (100 mL). The organic layer was separated and the aqueous layer was extracted with additional ethyl acetate. The combined organic layers were dried with magnesium sulfate, filtered, and concentrated under reduced pressure to provide the title compound: $^1$H NMR (CD$_3$OD): δ 1.43 (s, 9H), 1.8 (m, 1H), 2.07 (m, 1H), 2.53 (m, 2H), 2.73 (m, 1H), 2.81 (s, 3H), 2.60 (dd, J=27 Hz, J=15 Hz, 2H), 4.71 (m, 1H), 7.32 (m, 5H). MS (DCl/NH$_3$) m/z 291 (M+H)$^+$.

Example 2B tert-butyl methyl[(3R)-pyrrolidin-3-yl]carbamate

To a solution of the product of Example 2A (285 mg, 0.98 mmol) in 4.4% formic acid/methanol (20 mL) under a nitrogen atmosphere was added palladium hydroxide on carbon (20%, 40 mg) and the resulting mixture was heated at 60° C. for 16 hours. The mixture was cooled to room temperature, filtered through a layer of diatomaceous earth, washed with extra methanol (30 mL) and concentrated under reduced pressure. The residue was diluted with dichloromethane (30 mL), washed with 1 M sodium hydroxide, dried (magnesium sulfate), filtered and concentrated under reduced pressure to provide the title compound: $^1$H NMR (CD$_3$OD) δ 1.46 (s, 9H), 1.79 (m, 1H), 1.99 (m, 1H), 2.76 (m, 1H), 2.79 (s, 3H), 2.87 (m, 1H), 3.03 (m, 2H), 4.57 (p, J=6 Hz, 1H); MS (DCl/NH$_3$) m/z 201 (M+H)$^+$.

Example 2C tert-butyl (3R)-1-(2-amino-5,6,7a,8,9,10,11,11a-octahydro[1]benzofuro[2,3-h]quinazolin-4-yl)pyrrolidin-3-yl(methyl)carbamate The title product was prepared using the procedure outlined in the Example 1E, substituting the product from Example 2B for piperazine to provide the title product.

Example 2D

4-[(3R)-3-(methylamino)pyrrolidin-1-yl]-5,6,7a,8,9,10,11,11a-octahydro[1]benzofuro[2,3-h]quinazolin-2-amine A solution of the product from Example 2C (51 mg, 0.115 mmol) in dichloromethane (2 mL) was treated with trifluoroacetic acid (0.18 mL) at ambient temperature and stirred for 16 hours. The mixture was diluted with dichloromethane (20 mL) and basified with sodium hydroxide (1 N). The organic layer was separated, dried with magnesium sulfate, and concentrated under reduced pressure. The resulting residue was chromatographed on a silica gel column eluting with ammonium hydroxide/methanol/dichloromethane (0.8/8/92) to provide the title product: $^1$H NMR (CD$_3$OD) δ 1.10-1.22 (m, 1H), 1.25-1.36 (m, 1H), 1.42-1.55 (m, 1H), 1.56-1.68 (m, 2H), 1.78-1.90 (m, 1H), 1.95-2.07 (m, 2H), 2.11-2.31 (m, 2H), 2.48 (t, 2H), 2.55-2.60 (m, 3H), 2.98-3.09 (m, 3H), 3.49-3.56 (m, 1H), 3.65-3.77 (m, 2H), 3.80-3.91 (m, 2H), 4.68-4.75 (m, 1H); MS (DCl/NH$_3$) m/z 342 (M+H)$^+$.

Example 3

(−)-(7aS*,11aS*)-4-piperazin-1-yl-5,6,7a,8,9,10,11,11a-octahydro[1]benzofuro[2,3-h]quinazolin-2-amine Example 3A (−)-tert-butyl 4-[(7aS*,11aS*)-2-amino-5,6,7a,8,9,10,11,11a-octahydro[1]benzofuro[2,3-h]quinazolin-4-yl]piperazine-1-carboxylate A solution of the product from Example 1D (750 mg, 1.814 mmol) and tert-butyl piperazine-1-carboxylate (2027 mg, 10.88 mmol) in acetonitrile (15 mL) in a sealed tube was heated with an oil bath to 125° C. for 16 hours. The mixture was diluted with dichloromethane (60 mL), washed with water, dried with magnesium sulfate and concentrated. The residue was chromatographed on silica gel column eluting with 10-50% ethyl acetate/hexane to provide a light yellowish solid as the racemate, which was then separated on preparatory Chiralpack™ AD column eluting with a gradient of 5-35% isopropanol/hexane over 35 minutes, to provide the title compound as the faster eluting enantiomer (The retention time of this enantiomer was about 16 minutes): $[\alpha]_{589}^{20}$ −112° (c 0.010, methanol).

Example 3B (−)-(7aS*,11aS*)-4-piperazin-1-yl-5,6,7a,8,9,10,11,11a-octahydro[1]benzofuro[2,3-h]quinazolin-2-amine The product from Example 3A (179 mg, 0.419 mmol) was cooled with an ice bath and treated with trifluoroacetic acid (6.5 mL, 84 mmol) for 1 minute, then concentrated under reduced pressure for about 2 minutes to remove excess trifluoroacetic acid. The residue was cooled with an ice bath, taken up in dichloromethane (50 mL) and basified with sodium hydroxide (10%). The organic layer was separated, dried with magnesium sulfate, and concentrated under reduced pressure. The resulting residue was chromatographed on a silica gel column eluting with ammonium hydroxide/methanol/dichloromethane (0.8/8/92) to provide the title product in enantiomerically enriched form: $^1$H NMR (CDCl$_3$) δ 1.20-1.31 (m, 2H), 1.44-1.53 (m, 1H), 1.53-1.61 (m, 2H), 1.71-1.85 (m, 1H), 2.08-2.16 (m, 2H), 2.42 (t, 2H), 2.67-2.78 (m, 2H), 2.93-3.00 (m, 4H), 3.03-3.10 (m, 1H), 3.10-3.16 (m, 4H), 4.62-4.69 (m, 3H); MS (DCl/NH$_3$) m/z 328 (M+H)$^+$; $[\alpha]_{589}^{20}$ −106° (c 0.0038, methanol).

Example 4

(+)-(7aR*,11aR*)-4-piperazin-1-yl-5,6,7a,8,9,10,11,11a-octahydro[1]benzofuro[2,3-h]quinazolin-2-amine Example 4A (+)-tert-butyl 4-[(7aR*,11aR*)-2-amino-5,6,7a,8,9,10,11,11a-octahydro[1]benzofuro[2,3-h]quinazolin-4-yl]piperazine-1-carboxylate By application of the procedure described in Example 3A, after separation on a preparatory Chiralpack™ AD column eluting with a gradient of 5-35% isopropanol/hexane over 35 minutes, the title compound was obtained as the slower eluting enantiomer (The retention time of this enantiomer was about 21 minutes.): $[\alpha]_{589}^{20}$+91° (c 0.010, methanol).

Example 4B (+)-(7aR*,11aR*)-4-piperazin-1-yl-5,6,7a,8,9,10,11,11a-octahydro[1]benzofuro[2,3-h]quinazolin-2-amine The title product was prepared using the procedure described in Example 3B substituting the product from Example 4A for the product from Example 3A to provide the title product in enantiomerically enriched form: $^1$H NMR (CDCl$_3$) δ 1.19-1.31 (m, 2H), 1.46-1.53 (m, 1H), 1.54-1.59 (m, 2H), 1.74-1.84 (m, 1H), 2.07-2.15 (m, 2H), 2.4 (t, 2H), 2.69-2.77 (m, 2H), 2.93-2.99 (m, 4H), 3.02-3.10 (m, 1H), 3.10-3.15 (m, 4H), 4.53-4.59 (m, 2H), 4.63-4.68 (m, 1H); MS (DCl/NH$_3$) m/z 328 (M+H)$^+$ $[\alpha]_{589}^{20}$+368° (c 0.0038, methanol).

Example 5

4-(4-methyl-1,4-diazepan-1-yl)-5,6,7a,8,9,10,11,11a-octahydro[1]benzofuro[2,3-h]quinazolin-2-amine The title product was prepared using the procedure outlined in Example 1E substituting N-methylhomopiperazine for piperazine to provide the title product: $^1$H NMR (CDCl$_3$) δ 1.22-1.31 (m, 2H), 1.50-1.55 (m, 1H), 1.74-1.84 (m, 1H), 1.89-1.98 (m, 2H), 2.06-2.15 (m, 2H), 2.36-2.43 (m, 3H), 2.37-2.39 (m, 3H), 2.53-2.60 (m, 1H), 2.59-2.65 (m, 2H), 2.70 (t, 2H), 2.79 (t, 2H), 3.00-3.09 (m, 1H), 3.52 (t, 2H), 3.55-3.60 (m, 2H), 4.43-4.49 (m, 2H), 4.61-4.68 (m, 1H); MS (DCl/NH$_3$) m/z 356 (M+H)$^+$.

Example 6

4-(4-methylpiperazin-1-yl)-5,6,7a,8,9,10,11,11a-octahydro[1]benzofuro[2,3-h]quinazolin-2-amine The title product was prepared using the procedure described in Example 1E substituting 1-methylpiperazine for piperazine to provide the title product: $^1$H NMR (CDCl$_3$) δ 1.22-1.33 (m, 2H), 1.73-1.85 (m, 1H), 2.07-2.16 (m, 2H), 2.32-2.34 (m, 3H), 2.34-2.39 (m, 1H), 2.42 (t, 4H), 2.51 (t, 4H), 2.73 (t, 2H), 3.01-3.12 (m, 1H), 3.21 (t, 4H), 4.50-4.59 (m, 2H), 4.62-4.70 (m, 1H); MS (DCl/NH$_3$) m/z 342 (M+H)$^+$.

Example 7

4-[(3R)-3-aminopyrrolidin-1-yl]-7a,8,9,10,11,11a-hexahydro[1]benzofuro[2,3-h]quinazolin-2-amine

Example 7A tert-butyl (3R)-1-(2-amino-5,6,7a,8,9,10,11,11a-octahydro[1]benzofuro[2,3-h]quinazolin-4-yl)pyrrolidin-3-ylcarbamate The title product was prepared using the procedure described in Example 1E substituting (R)-tert-butyl pyrrolidin-3-ylcarbamate for piperazine.

Example 7B

4-[(3R)-3-aminopyrrolidin-1-yl]-7a,8,9,10,11,11a-hexahydro[1]benzofuro[2,3-h]quinazolin-2-amine A solution of the product from Example 7A (28 mg, 0.065 mmol) in dichloromethane (2 mL) was treated with trifluoroacetic acid (0.2 mL) at ambient temperature and stirred for 16 hours. The mixture was diluted with dichloromethane (20 mL), and basified with sodium hydroxide (1 N). The organic layer was separated, dried with magnesium sulfate, and concentrated under reduced pressure. The resulting residue was chromatographed on a silica gel column eluting with ammonium hydroxide/methanol/dichloromethane (0.8/8/92) to provide the dehydrogenated material as the major product and title compound: $^1$H NMR (CD$_3$OD) δ 1.00-1.18 (m, 1H), 1.27-1.41 (m, 1H), 1.45-1.58 (m, 1H), 1.62-1.75 (m, 2H), 1.92-2.07 (m, 3H), 2.11-2.24 (m, 1H), 2.24-2.39 (m, 2H), 3.38-3.52 (m, 1H), 3.74-3.92 (m, 2H), 3.98-4.12 (m, 1H), 4.10-4.24 (m, 2H), 6.87 (d, 1H), 8.08 (d, 1H); MS (DCl/NH$_3$) m/z 326 (M+H)$^+$.

Example 8

4-[(1R,5S)-3,6-diazabicyclo[3.2.0]hept-6-yl]-7a,8,9,10,11,11a-hexahydro[1]benzofuro[2,3-h]quinazolin-2-amine

Example 8A benzyl(1S,5S)-6-(2-amino-5,6,7a,8,9,10,11,11a-octahydro[1]benzofuro[2,3-h]quinazolin-4-yl-3,6-diazabicyclo[3.2.0]heptane-3-carboxylate The title product was prepared using the procedures described in Example 1E substituting (1S,5S)-3,6-diaza-bicyclo[3.2.0]heptane-3-carboxylic acid benzyl ester (CAS#370881-43-9, prepared according US2006035937A1) for piperazine.

Example 8B

4-[(1R,5S)-3,6-diazabicyclo[3.2.0]hept-6-yl]-7a,8,9,10,11,11a-hexahydro[1]benzofuro[2,3-h]quinazolin-2-amine A solution of the product of Example 8A (90 mg, 0.190 mmol) in ethanol (8 mL) was treated with palladium on carbon (10%) (202 mg, 0.190 mmol), placed under an atmosphere of hydrogen, and stirred at ambient temperature for 16 hours. The mixture was filtered through a layer of diatomaceous earth, washed with a small amount of ethanol and concentrated under reduced pressure. The resulting residue was chromatographed on silica gel column eluting with ammonium hydroxide/methanol/dichloromethane (0.8/8/92) to provide the title product: $^1$H NMR (CD$_3$OD) δ 0.84-0.96 (m, 1H), 1.59-1.71 (m, 2H), 2.08-2.20 (m, 2H), 2.23-2.32 (m, 1H), 2.36-2.46 (m, 1H), 2.69-2.86 (m, 2H), 2.98-3.09 (m, 2H), 3.18-3.25 (m, 2H), 3.36-3.46 (m, 1H), 3.50-3.56 (m, 1H), 4.16-4.32 (m, 1H), 6.75 (d, 1H), 7.68 (d, 1H); MS (DCl/NH$_3$) m/z 338 (M+H)$^+$.

Example 9

4-(1,4-diazepan-1-yl)-5,6,7a8,9,10,11,11a-octahydro[1]benzofuro[2,3-h]quinazolin-2-amine The title product was prepared using the procedure outlined in the Example 1E substituting homopiperazine for piperazine: $^1$H NMR (CDCl$_3$) δ 1.22-1.34 (m, 2H), 1.48-1.88 (m, 6H), 2.06-2.17 (m, 2H), 2.41 (t, J=8.13 Hz, 2H), 2.75-2.84 (m, J=8.33, 8.33 Hz, 2H), 2.94 (t, 2H), 2.99-3.08 (m, 3H), 3.47-3.56 (m, 4H), 4.49 (s, 2H), 4.61-4.69 (m, 1H); MS (DCl/NH$_3$) m/z 342 (M+H)$^+$.

Example 10

4-(4-isopropyl-1,4-diazepan-1-yl)-5,6,7a,8,9,10,11,11a-octahydro[1]benzofuro[2,3-h]quinazolin-2-amine A solution of the product of Example 9 (50 mg, 0.146 mmol) in dichloromethane (250 mL) was treated with acetone (0.022 mL, 0.293 mmol) and stirred for 5 minutes. This mixture was treated with sodium triacetoxyborohydride (65.3 mg, 0.293 mmol) at room temp and stirred for 16 hours. The mixture was diluted with dichloromethane (40 mL), washed with saturated aqueous sodium bicarbonate solution, dried with magnesium sulfate, and concentrated under reduced pressure. The resulting residue was chromatographed on a silica gel column eluting with ammonium hydroxide/methanol/dichloromethane (0.4/4/96) to provide the title product: $^1$H NMR (CDCl$_3$) δ 1.08 (d, J=6.44 Hz, 6H), 1.14-1.30 (m, 2H), 1.49-1.63 (m, 3H), 1.76-1.86 (m, 1H), 1.96-2.02 (m, 2H), 2.07-2.17 (m, 2H), 2.41 (t, J=8.65 Hz, 2H), 2.74-2.83 (m, 4H), 2.86-2.93 (m, 2H), 3.04-3.14 (m, 1H), 3.15-3.25 (m, 1H), 3.55 (t, J=6.10 Hz, 2H), 3.62-3.67 (m, 2H), 4.63-4.70 (m, 1H), 5.49-5.59 (m, 2H); MS (DCl/NH$_3$) m/z 384 (M+H)$^+$.

Example 11

4-(4-cyclobutyl-1,4-diazepan-1-yl)-5,6,7a,8,9,10,11,11a-octahydro[1]benzofuro[2,3-h]quinazolin-2-amine The title product was prepared using the procedure outlined in the Example 10 substituting cyclobutanone for acetone: $^1$H NMR (CDCl$_3$) δ 1.01-1.15 (m, 1H), 1.19-1.32 (m, 1H), 1.39-1.52 (m, 1H), 1.54-1.65 (m, 3H), 1.69-1.84 (m, 2H), 2.04-2.19 (m, 8H), 2.43 (t, J=8.48 Hz, 2H), 2.59-2.67 (m, 2H), 2.76-2.85 (m, 4H), 2.99 (q, 1H), 3.33 (q, J=7.46 Hz, 1H), 3.59 (t, J=6.27 Hz, 2H), 3.68-3.75 (m, 2H), 4.65-4.73 (m, 1H), 6.39-6.68 (m, 2H); MS (DCl/NH$_3$) m/z 396 (M+H)$^+$.

Example 12 trans-4-piperazin-1-yl-5,6,6a,7,8,9,10,10a-octahydrobenzo[h]quinazolin-2-amine

Example 12A methyl 1-oxodecahydronaphthalene-2-carboxylate

A suspension of sodium hydride (4.60 g, 115 mmol) in tetrahydrofuran (20 mL) was treated with dimethyl carbonate (8.29 mL, 99 mmol), heated to reflux under nitrogen, treated dropwise with a solution of octahydronaphthalen-1(2H)-one (Aldrich cat#115063, mixture of trans (major) and cis (minor), 5 g, 32.8 mmol) in tetrahydrofuran (20 mL) over 5 minutes, and heated to reflux overnight. The mixture was cooled, diluted with ether (300 mL) and treated with 1 M hydrochloric acid (150 mL). The layers were separated and the aqueous layer was extracted with ether (2×100 mL). The combined ether layers were washed with brine, dried (magnesium sulfate), filtered and concentrated to provide the desired product that was not purified, but used as is in the next step.

Example 12B

2-amino-5,6,6a,7,8,9,10,10a-octahydrobenzo[h]quinazolin-4-ol

In a 500 mL round bottomed flask, a suspension of guanidine carbonate (11.1 g, 61.4 mmol) in N,N-dimethylformamide (100 mL) was heated with stirring to 160° C. for 10 minutes, and a solution of the product from Example 12A (6.46 g, 30.7 mmol) in N,N-dimethylformamide (15 mL) was added dropwise over 2 minutes. The flask that contained the product from Example 12A was rinsed with an additional 10 mL of N,N-dimethylformamide and this was added to the reaction over 2 minutes. The reaction was heated to 165° C. for 20 minutes, cooled to room temperature and partitioned between 1 M sodium hydroxide (650 mL) and ether (200 mL). The layers were separated and the ether layer was extracted with 1 M sodium hydroxide (25 mL). The ether layer was disposed of. The combined aqueous sodium hydroxide layers were cooled in an ice bath and acidified to pH ~7 with concentrated hydrochloric acid. After standing at ambient temperature for 15 minutes, the resulting solid was collected by filtration, washed with water and dried overnight in a drying oven with heating under vacuum to provide the title compound: $^1$H NMR (DMSO-d$_6$) δ 0.78-0.96 (m, 1H), 1.00-1.35 (m, 5H), 1.61-1.74 (m, 3H), 1.75-192 (m, 2H), 2.01-2.18 (m, 1H), 2.28-2.58 (m, 2H), 6.13 (br s, 2H), 10.66 (s, 1H); MS (DCl/NH$_3$) m/z 220 (M+H)$^+$.

Example 12C trans-2-amino-5,6,6a,7,8,9,10,10a-octahydrobenzo[h]quinazolin-4-yl 4-nitrobenzenesulfonate A flask containing the product of Example 12B (7.07 g, 32.2 mmol) in dichloromethane (322 mL) under nitrogen was treated with 4-nitrobenzene-1-sulfonyl chloride (10.7 g, 48.4 mmol) and 4-(dimethylamino)pyridine (0.39 g, 3.2 mmol). The resulting suspension was treated with triethylamine (7.64 mL, 54.8 mmol) and stirred overnight. The mixture was partitioned between saturated aqueous sodium bicarbonate solution and dichloromethane (100 mL). The layers were separated and the aqueous layer was extracted with dichloromethane (250 mL). The combined dichloromethane layers were dried (magnesium sulfate), filtered, and concentrated. The residue was suspended on silica gel and chromatographed in two portions. For each of the two chromatographies, a DASi-65 Empty-NP drypac (Analogix, Burlington, Wis.) applications system was used to hold the residue-silica gel mixture and this was chromatographed on an Analogix IntelliFlash 280 using a SF40-150 g column eluting with 9:0 (5 minutes), 9:0 to 9:1 (15 minutes), 9:1 (10 minutes), 9:1 to 0:1 (15 minutes) and 0:1 (10 minutes) dichloromethane:ethyl acetate to provide the title compound as the major, less polar, product: $^1$H NMR (CDCl$_3$) δ0.96-1.24 (m, 2H), 1.25-1.47 (m, 4H), 1.72-1.94 (m, 4H), 2.03-2.14 (m, 1H), 2.44-2.64 (m, 2H), 2.68-2.79 (m, 1H), 4.70 (br s, 2H), 8.28 (d, J=9.1 Hz, 2H), 8.38-8.48 (m, J=8.7 Hz, 2H); MS (DCl/NH$_3$) m/z 405 (M+H)$^+$.

Example 12D cis-2-amino-5,6,6a,7,8,9,10,10a-octahydrobenzo[h]quinazolin-4-yl 4-nitrobenzenesulfonate The procedure from Example 12C provided the title compound as the minor, more polar, product: $^1$H NMR (DMSO-d$_6$) δ 1.22-2.02 (m, 12H), 2.31-2.44 (m, 1H), 2.55 (s, 1H), 6.62 (br s, 2H), 8.42 (d, J=2.4 Hz, 4H); MS (DCl/NH$_3$) m/z 405 (M+H)$^+$.

Example 12E trans-4-piperazin-1-yl-5,6,6a,7,8,9,10,10a-octahydrobenzo[h]quinazolin-2-amine The procedure from Example 13, substituting Example 12C for Example 12D, provided the title compound: $^1$H NMR (CDCl$_3$) δ1.05-1.58 (m, 6H), 1.73-1.85 (m, 3H), 1.87-1.97 (m, 1H), 2.14-2.25 (m, 1H), 2.36-2.65 (m, 3H), 2.92-3.03 (m, 2H), 3.05-3.15 (m, 2H), 3.43 (ddd, J=13.2, 6.8, 3.1 Hz, 2H), 3.68 (ddd, J=13.5, 6.9, 3.1 Hz, 2H), 6.04 (br s, 2H); MS (DCl/NH$_3$) m/z 288 (M+H)$^+$.

Example 13 cis-4-piperazin-1-yl-5,6,6a,7,8,9,10,10a-octahydrobenzo[h]quinazolin-2-amine

Example 13A tert-butyl 4-[cis-2-amino-5,6,6a,7,8,9,10,10a-octahydrobenzo[h]quinazolin-4-yl]piperazine-1-carboxylate A flask containing the product of Example 12D (370 mg, 0.92 mmol) in 2-methoxyethanol (3.7 mL) was treated with tert-butyl piperazine-1-carboxylate (511 mg, 2.7 mmol) and Hunig's base (1.1 mL, 6.4 mmol), sealed with a glass stopper, heated to 110° C. overnight, cooled and partitioned between 1 M sodium hydroxide (10 mL) and dichloromethane (50 mL). The aqueous layer was further extracted with dichloromethane (2×50 mL). The combined dichloromethane layers were dried (magnesium sulfate), filtered, concentrated and chromatographed on an Analogix IntelliFlash 280 using a SF15-24 g column eluting with 9:0 (5 minutes), 9:0 to 9:1 (5 minutes), 9:1 (5 minutes), 9:1 to 0:1 (20 minutes) dichloromethane:ethyl acetate to provide the title compound: $^1$H NMR (CDCl$_3$) δ 1.33-1.60 (m, 4H), 1.48 (s, 9H), 1.60-1.70 (m, 4H), 1.76-1.96 (m, 2H), 2.04 (m, 1H), 2.39-2.63 (m, 3H), 3.14 (ddd, J=12.2, 6.4, 3.1 Hz, 2H), 3.24-3.35 (m, 2H), 3.41-3.60 (m, 4H), 4.56 (br s, 2H); MS (DCl/NH$_3$) m/z 388 (M+H)$^+$.

Example 13B cis-4-piperazin-1-yl-5,6,6a,7,8,9,10,10a-octahydrobenzo[h]quinazolin-2-amine The product of Example 13A (0.35 g, 0.90 mmol) was treated with trifluoroacetic acid (6 mL), heated to 60° C. for 1 minute, concentrated, and chromatographed on an Analogix IntelliFlash 280 using a SF15-24 g column eluting with 2% (5 minutes) and then 2-20% (over 20 minutes) (9:1 methanol: ammonium hydroxide) in dichloromethane to provide the title compound: $^1$H NMR (CDCl$_3$) δ 1.32-2.10 (m, 11H), 2.39-2.64 (m, 3H), 2.86-3.05 (m, 4H), 3.16 (ddd, J=12.9, 6.4, 2.7 Hz, 2H), 3.33 (ddd, J=12.6, 6.7, 3.1 Hz, 2H), 4.64 (s, 2H); MS (DCl/NH$_3$) m/z 288 (M+H)$^+$.

Example 14 trans-4-[3-(methylamino)azetidin-1-yl]-5,6,6a,7,8,9,10,10a-octahydrobenzo[h]quinazolin-2-amine bis(trifluoroacetate)

Example 14A tert-butyl 1-[trans-2-amino-5,6,6a,7,8,9,10,10a-octahydrobenzo[h]quinazolin-4-yl]azetidin-3-yl(methyl)carbamate In a capped vial, a mixture of the product of Example 12C (100 mg, 0.25 mmol), tert-butyl azetidin-3-yl(methyl)carbamate (69 mg, 0.37 mmol), triethylamine (0.12 mL, 0.88 mmol) and ethanol (0.5 mL) was heated overnight at 80° C. The mixture was cooled and partitioned between 1 M sodium hydroxide (5 mL) and dichloromethane (25 mL). The layers were separated and the aqueous layer was extracted with dichloromethane (25 mL). The combined dichloromethane layers were dried (magnesium sulfate), filtered, concentrated and chromatographed on an Analogix IntelliFlash 280 using a SF10-4 g column eluting with 9:1 (5 minutes), 9:1 to 0:1 (10 minutes) and 0:1 (10 minutes) dichloromethane:ethyl acetate to provide the title compound: $^1$H NMR (CDCl$_3$) δ 0.94-1.43 (m, 6H), 1.46 (s, 9H), 1.61-1.69 (m, 1H), 1.70-1.81 (m, 3H), 1.83-1.92 (m, 1H), 1.96-2.07 (m, 1H) 2.43-2.52 (m, 2H), 2.57-2.66 (m, 1H), 2.92 (s, 3H), 4.01 (dd, J=9.0, 5.9 Hz, 1H), 4.20 (d, J=6.8 Hz, 2H), 4.40 (t, J=8.5 Hz, 1H), 4.51 (s, 2H); MS (DCl/NH$_3$) m/z 388 (M+H)$^+$.

Example 14B trans-4-[3-(methylamino)azetidin-1-yl]-5,6,6a,7,8,9,10,10a-octahydrobenzo[h]quinazolin-2-amine bis(2,2,2-trifluoroacetate)

A flask containing the product of Example 14A (86 mg, 0.22 mmol) was treated with trifluoroacetic acid (2 mL), heated to 60° C. for 2 minutes and concentrated. The residue was dissolved in dichloromethane (3 mL) and methanol (5 drops) and a solid crystallized. The solid was collected by filtration, washed with dichloromethane and dried under vacuum overnight to provide the title compound as the bis (trifluoroacetate): $^1$H NMR (DMSO-d$_6$) δ 0.96-1.47 (m, 6H), 1.73 (d, J=9.8 Hz, 3H), 1.86 (d, J=11.9 Hz, 1H), 2.28 (m, 2H), 2.61 (s, 3H), 4.06 (m, 1H), 4.13-4.99 (m, 4H), 7.51 (br s, 2H), 9.33 (br s, 2H), 11.47 (br s, 1H); MS (DCl/NH$_3$) m/z 288 (M+H)$^+$.

Example 15 trans-4-[3-(ethylamino)azetidin-1-yl]-5,6,6a,7,8,9,10,10a-octahydrobenzo[h]quinazolin-2-amine bis(trifluoroacetate)

The procedure from Example 14, substituting tert-butyl azetidin-3-yl(ethyl)carbamate for tert-butyl azetidin-3-yl (methyl)carbamate, provided the title compound as the bis (trifluoroacetate): $^1$H NMR (DMSO-d6) δ 0.97-1.46 (m, 6H), 1.19 (t, J=7.1 Hz, 3H), 1.68-1.79 (m, 3H), 1.82-1.91 (m, 1H), 2.21-2.35 (m, 2H), 2.94-3.05 (m, 2H), 4.05-4.50 (m, 3H), 4.56-5.01 (m, 2H), 7.52 (br s, 2H), 9.35 (br s, 2H), 11.45 (br s, 1H); MS (DCl/NH$_3$) m/z 302 (M+H)$^+$.

Example 16 trans-4-[(3R)-3-(methylamino)pyrrolidin-1-yl]-5,6,
6a,7,8,9,10,10a-octahydrobenzo[h]quinazolin-2-
amine

Example 16A tert-butyl (3R)-1-[trans-2-amino-5,6,6a,7,8,9,10,10a-
octahydrobenzo[h]quinazolin-4-yl]pyrrolidin-3-yl
(methyl)carbamate In a capped vial, a mixture of the product of Example 12C (100 mg, 0.25 mmol), (R)-tert-butyl methyl(pyrrolidin-3-yl) carbamate (74 mg, 0.37 mmol), triethylamine (0.12 mL, 0.88 mmol) and ethanol (0.5 mL) was heated overnight at 80° C. The mixture was cooled and partitioned between 1 M sodium hydroxide (5 mL) and dichloromethane (25 mL). The layers were separated and the aqueous layer was extracted with dichloromethane (25 mL). The combined dichloromethane layers were dried (magnesium sulfate), filtered, concentrated and chromatographed on an Analogix IntelliFlash 280 using a SF10-4 g column eluting with 9:1 (5 minutes), 9:1 to 0:1 (10 minutes) and 0:1 (10 minutes) dichloromethane:ethyl acetate to provide the title compound: $^1$H NMR (CDCl$_3$) δ 0.97-1.21 (m, 2H), 1.22-1.42 (m, 4H), 1.47 (s, 9H), 1.67-2.18 (m, 8H), 2.49-2.75 (m, 3H), 2.80 and 2.83 (s and s, 3H), 3.34-3.44 (m, 1H), 3.46-3.73 (m, 2H), 3.89-3.99 (m, 1H), 4.50 (s, 2H); MS (DCl/NH$_3$) m/z 402 (M+H)$^+$.

Example 16B trans-4-[(3R)-3-(methylamino)pyrrolidin-1-yl]-5,6,
6a,7,8,9,10,10a-octahydrobenzo[h]quinazolin-2-
amine A flask containing the product of Example 16A (103 mg, 0.26 mmol) was treated with trifluoroacetic acid (2 mL), heated to 60° C. for 2 minutes, concentrated and chromatographed on an Analogix IntelliFlash 280 using a SF10-4 g column eluting with 2% (5 minutes) and 2-20% (over 20 minutes) (9:1 methanol:ammonium hydroxide) in dichloromethane to provide the title compound: $^1$H NMR (CDCl$_3$) δ 0.96-1.50 (m, 7H), 1.55-1.69 (m, 1H), 1.69-1.81 (m, 3H), 1.83-1.95 (m, 2H), 1.97-2.08 (m, 1H), 2.44 and 2.48 (s and s, 3H), 2.54-2.76 (m, 3H), 3.16-3.59 (m, 3H), 3.63-3.93 (m, 2H), 4.48 (br s, 2H); MS (DCl/NH$_3$) m/z 302 (M+H)$^+$.

Example 17 trans-4-[(3R)-3-aminopyrrolidin-1-yl]-5,6,6a,7,8,9,
10,10a-octahydrobenzo[h]quinazolin-2-amine The procedure described in Example 16 was applied, substituting (R)-tert-butyl pyrrolidin-3-ylcarbamate for (R)-tert-butyl methyl(pyrrolidin-3-yl)carbamate to provide the title compound: $^1$H NMR (CDCl$_3$) δ 0.94-2.21 (m, 15H), 2.52-2.77 (m, 3H), 3.19-4.01 (m, 5H), 4.48 (br s, 2H); MS (DCl/NH$_3$) m/z 288 (M+H)$^+$.

Example 18 trans-4-[cis-octahydro-6H-pyrrolo[3,4-b]pyridin-6-
yl]-5,6,6a7,8,9,10,10a-octahydrobenzo[h]quinazolin-
2-amine The procedure described in Example 16 was applied, substituting cis-tert-butyl octahydro-1H-pyrrolo[3,4-b]pyridine-1-carboxylate for (R)-tert-butyl methyl(pyrrolidin-3-yl)carbamate to provide the title compound: $^1$H NMR (CDCl$_3$) δ 0.94-1.52 (m, 8H), 1.55-1.83 (m, 6H), 1.83-1.92 (m, 1H), 1.96-2.07 (m, 1H), 2.11-2.27 (m, 1H) 2.56-2.77 (m, 4H), 2.90-3.07 (m, 1H), 3.25-3.31 (m, 1H), 3.37-3.50 (m, 2H), 3.80-3.95 (m, 2H), 4.45 (br s, 2H); MS (DCl/NH$_3$) m/z 328 (M+H)$^+$.

Example 19 cis-4-[(3R)-3-(methylamino)pyrrolidin-1-yl]-5,6,6a,
7,8,9,10,10a-octahydrobenzo[h]quinazolin-2-amine The procedure from Example 16, substituting the product of Example 12D for the product of Example 12C, provided the title compound: $^1$H NMR (CDCl$_3$) δ 1.31-2.18 (m, 14H), 2.45 and 2.48 (s and s, 3H), 2.49-2.82 (m, 3H), 3.17-3.29 (m, 1H), 3.35-3.47 (m, 1H), 3.51-3.86 (m, 3H), 4.45 (br s, 2H); MS (DCl/NH$_3$) m/z 302 (M+H)$^+$.

Example 20 cis-4-[(3R)-3-aminopyrrolidin-1-yl]-5,6,6a,7,8,9,10,
10a-octahydrobenzo[h]quinazolin-2-amine The procedure from Example 16 was applied, substituting the product of Example 12D for the product of Example 12C, and substituting (R)-tert-butyl pyrrolidin-3-ylcarbamate for (R)-tert-butyl methyl(pyrrolidin-3-yl)carbamate to provide the title compound: $^1$H NMR (CDCl$_3$) δ 1.17-2.17 (m, 15H), 2.47-2.82 (m, 3H), 3.25-3.39 (m, 1H), 3.48-3.94 (m, 4H), 4.44 (s, 2H); MS (DCl/NH$_3$) m/z 288 (M+H)$^+$.

Example 21 cis-4-[cis-octahydro-6H-pyrrolo[3,4-b]pyridin-6-yl]-
5,6,6a,7,8,9,10,10a-octahydrobenzo[h]quinazolin-2-
amine The procedure from Example 16 was applied, substituting the product of Example 12D for the product of Example 12C, and substituting cis-tert-butyl octahydro-1H-pyrrolo[3,4-b] pyridine-1-carboxylate for (R)-tert-butyl methyl(pyrrolidin-3-yl)carbamate to provide the title compound: $^1$H NMR (CD$_3$OD) δ 1.31-1.87 (m, 12H), 1.89-2.00 (m, 3H), 2.17-2.33 (m, 1H), 2.41-2.53 (m, 1H), 2.56-2.83 (m, 2H), 2.84-2.99 (m, 2H), 3.21-3.47 (m, 1H), 3.50-3.94 (m, 4H); MS (DCl/NH$_3$) m/z 328 (M+H)$^+$.

Example 22 cis-4-[3-(methylamino)azetidin-1-yl]-5,6,6a,7,8,9,
10,10a-octahydrobenzo[h]quinazolin-2-amine The procedure from Example 16 was applied, substituting the product of Example 12D for the product of Example 12C, and substituting tert-butyl azetidin-3-yl(methyl)carbamate for (R)-tert-butyl methyl(pyrrolidin-3-yl)carbamate to provide the title compound: $^1$H NMR (CDCl$_3$) δ 1.29-1.71 (m, 9H), 1.80-2.00 (m, 3H), 2.36-2.62 (m, 3H), 2.42 (s, 2H), 3.57 (m, 1H), 3.81 (dd, J=8.8, 5.1 Hz, 1H), 3.90 (dd, J=9.0, 5.3 Hz, 1H), 4.26-4.33 (m, 1H), 4.34-4.41 (m, 1H), 4.48 (s, 2H); MS (DCl/NH$_3$) m/z 288 (M+H)$^+$.

Example 23 cis-4-[3-(ethylamino)azetidin-1-yl]-5,6,6a,7,8,9,10,
10a-octahydrobenzo[h]quinazolin-2-amine The procedure from Example 16 was applied, substituting the product of Example 12D for the product of Example 12C, and substituting tert-butyl azetidin-3-yl(ethyl)carbamate for (R)-tert-butyl methyl(pyrrolidin-3-yl)carbamate to provide the title compound: $^1$H NMR (CDCl$_3$) δ 1.12 (t, J=7.1 Hz, 3H), 1.32-1.72 (m, 9H), 1.79-2.00 (m, 3H), 2.36-2.60 (m, 3H), 2.65 (q, J=7.1 Hz, 2H), 3.61-3.71 (m, 1H), 3.81 (dd, J=8.8, 5.4 Hz, 1H), 3.89 (dd, J=9.2, 5.8 Hz, 1H), 4.27-4.33 (m, 1H), 4.35-4.42 (m, 1H), 4.48 (s, 2H); MS (DCl/NH$_3$) m/z 302 (M+H)$^+$.

Example 24

4-cis-octahydro-6H-pyrrolo[3,4-b]pyridin-6-yl-6,7,
7a,8,11,11a-hexahydro-5H-8,11-ethanobenzo[6,7]
cyclohepta[1,2-d]pyrimidin-2-amine

Example 24A 1,4,4a,6,7,8,9,9a-octahydro-5H-1,4-ethanobenzo[7]
annulen-5-one

To a solution of (Z)-cyclohept-2-enone (1.4 g, 10 mmol) in dry toluene was added aluminum chloride (0.67 g, 5 mmol) and the resulting mixture was stirred at room temperature for 40 minutes. A solution of cyclohexadiene (9.62 g, 120 mmol) in toluene was added dropwise, and the mixture was stirred overnight at 40° C. The reaction mixture was filtered through diatomaceous earth and then partition in ethyl acetate/water. The organic layer was washed with sodium bicarbonate solution, dried (magnesium sulfate), filtered, evaporated under vacuum and purified by chromatography on silica gel eluting with 5-10% ether/hexane to provide the title compound: MS (DCl/NH$_3$) m/z 191 (M+H)$^+$, 208 (M+NH$_4$)$^+$.

Example 24B methyl 5-oxo-4,4a,5,6,7,8,9,9a-octahydro-1H-1,4-
ethanobenzo[7]annulene-6-carboxylate To a suspension of sodium hydride (0.60 g, 14.7 mmol) in dry tetrahydrofuran was added dimethylcarbonate (1.14 g, 12.6 mmol). The product from Example 24A (0.80 g, 4.2 mmol) in tetrahydrofuran was added dropwise and the mixture was heated at reflux for 6 hours, cooled, poured into 1 M hydrochloric acid and extracted with ether. The ether layer was dried (magnesium sulfate), filtered, concentrated and chromatographed on silica gel eluting with 20% ethyl acetate/hexane to provide the title compound: MS (DCl/NH$_3$) m/z 266 (M+NH$_4$)$^+$.

Example 24C 2-amino-6,7,7a,8,11,11a-hexahydro-5H-8,11-etha-
nobenzo[6,7]cyclohepta[1,2-d]pyrimidin-4-ol A mixture of Example 24B (0.85 g, 3.4 mmol), guanidine nitrate (0.84 g, 6.8 mmol) and potassium carbonate (0.95 g, 6.8 mmol) in N,N-dimethylformamide (5 mL) was heated to 110° C. overnight, cooled, diluted with water (20 mL), acidified to pH-7 with acetic acid, and a solid was isolated by filtration. This solid was absorbed onto silica gel then purified by chromatography on silica gel eluting with 10-20% ethanol/dichloromethane to provide the title compound: MS (DCl/NH$_3$) m/z 258 (M+H)$^+$.

Example 24D 2-amino-6,7,7a,8,11,11a-hexahydro-5H-8,11-etha-
nobenzo[6,7]cyclohepta[1,2-d]pyrimidin-4-yl 4-me-
thylbenzenesulfonate A mixture of the product of Example 24C (0.27 g, 1.0 mmol), 4-methylbenzene-1-sulfonyl chloride (0.40 g, 2.1 mmol), and triethylamine (0.44 mL, 3.2 mmol) in chloroform (5 mL) was treated with a small amount of 4-(dimethylamino)pyridine (10 mg) and stirred at room temperature overnight. The mixture was diluted with dichloromethane and washed with water. The organic layer was dried (magnesium sulfate), evaporated and chromatographed on silica gel eluting with 2-7% ethanol/dichloromethane to provide the title compound: MS (DCl/NH$_3$) m/z 412 (M+H)$^+$.

Example 24E 4-cis octahydro-6H-pyrrolo[3,4-b]pyridin-6-yl-6,7,
7a,8,11,11a-hexahydro-5H-8,11-ethanobenzo[6,7]
cyclohepta[1,2-d]pyrimidin-2-amine The procedure from Example 16 was applied, substituting the product of Example 24D for the product of Example 12C, and substituting cis-tert-butyl octahydro-1H-pyrrolo[3,4-b]pyridine-1-carboxylate for (R)-tert-butyl methyl(pyrrolidin-3-yl)carbamate to provide the title compound: $^1$H NMR (CDCl$_3$) δ 0.73-1.81 (m, 10H), 1.83-1.98 (m, 1H), 2.09-2.51 (m, 4H), 2.55-3.66 (m, 11H), 3.74-3.94 (m, 1H), 4.39 (s, 1H), 4.46 (s, 1H), 5.96-6.05 (m, 0.75H), 6.16-6.24 (m, 0.25H), 6.41-6.52 (m, 1H); MS (DCl/NH$_3$) m/z 366 (M+H)$^+$.

Example 25

4-[(3R)-3-(methylamino)pyrrolidin-1-yl]-6,7,7a,8,
11,11a-hexahydro-5H-8,11-ethanobenzo[6,7]cyclo-
hepta[1,2-d]pyrimidin-2-amine The procedure from Example 16 was applied, substituting the product of Example 24D for the product of Example 12C to provide the title compound: MS (DCl/NH$_3$) m/z 340 (M+H)$^+$.

Example 26

4-piperazin-1-yl-6,7,7a,8,11,11a-hexahydro-5H-8,
11-ethanobenzo[6,7]cyclohepta[1,2-d]pyrimidin-2-
amine The procedure from Example 16 was applied, substituting the product of Example 24D for Example 12C, and substituting tert-butyl piperazine-1-carboxylate for (R)-tert-butyl methyl(pyrrolidin-3-yl)carbamate to provide the title compound: MS (DCl/NH$_3$) m/z 326 (M+H)$^+$.

Example 27

4-cis octahydro-6H-pyrrolo[3,4-b]pryridin-6-yl-6,7,7a,8,9,10,11,11a-octahydro-5H-8,11-ethanobenzo[6,7]cyclohepta[1,2-d]pyrimidin-2-amine

Example 27A 2-amino-6,7,7a,8,9,10,11,11a-octahydro-5H-8,11-ethanobenzo[6,7]cyclohepta[1,2-d]pyrimidin-4-yl 4-methylbenzenesulfonate The product from Example 24D (0.14 g, 0.34 mmol) was hydrogenated in methanol under an atmosphere of hydrogen using 10% palladium hydroxide on carbon as a catalyst. The reaction was filtered to remove the catalyst solids and the filtrate was concentrated and chromatographed on silica gel eluting with 5% methanol/dichloromethane to provide the title compound: MS (DCI/NH$_3$) m/z 414 (M+H)$^+$.

Example 27B 4-cis-octahydro-6H-pyrrolo[3,4-b]pyridin-6-yl-6,7,7a,8,9,10,11,11a-octahydro-5H-8,11-ethanobenzo[6,7]cyclohepta[1,2-d]pyrimidin-2-amine The procedure from Example 16 was applied, substituting the product of Example 27A for Example 12C, and substituting cis-tert-butyl octahydro-1H-pyrrolo[3,4-b]pyridine-1-carboxylate for (R)-tert-butyl methyl(pyrrolidin-3-yl)carbamate to provide the title compound: MS (DCI/NH$_3$) m/z 368 (M+H)$^+$.

Example 28

4-[(3R)-3-(methylamino)pyrrolidin-1-yl]-6,7,7a,8,9,10,11,11a-octahydro-5H-8,11-ethanobenzo[6,7]cyclohepta[1,2-d]pyrimidin-2-amine The procedure from Example 16 was applied, substituting the product of Example 27A for the product of Example 12C to provide the title compound: MS (DCI/NH$_3$) m/z 342 (M+H)$^+$.

Determination of Biological Activity

There are many methods available to show the effectiveness of compounds as histamine H$_4$ receptor ligands. Histamine H$_4$ receptors from mammalian species have been cloned. Methods to clone, express, and assess the potency and functional activity of such cloned genes are well known to those skilled in the art of molecular biology. Examples of methods of cloning and expressing histamine H$_4$ receptors, and of assessing the potency and functional activity are described in Nguyen, et al. Molecular Pharmacology (2001) vol. 59 pp. 427-433; Zhu, et al. Molecular Pharmacology (2001) vol. 59 pp. 434-441; Coge, et al., Biochemical and Biophysical Research Communications (2001) vol. 284, pp. 301-309; Liu, et al. Molecular Pharmacology (2001) vol. 59 pp. 420-426; Liu, et al. Journal of Pharmacology and Experimental Therapeutics (2001) v. 299, pp. 121-130; and Thurmond, et al. Journal of Pharmacology and Experimental Therapeutics (2004) v. 309, pp. 404-413. In the present case, to determine the potency and effectiveness of representative compounds of this invention as histamine-H$_4$ receptor ligands (H$_4$ receptor ligands), the following tests were conducted according to previously described methods (see Esbenshade, et al., Biochemical Pharmacology (2004), vol. 68, pp. 933-945, and in Krueger, et al., Journal of Pharmacology and Experimental Therapeutics (2005) v. 314, pp. 271-281): histamine H$_4$ receptors were cloned and stably expressed in HEK-293 (human embryonic kidney) cells coexpressing a Gαqi5. Before testing, cells are loaded with a Ca+$^2$ sensitive fluorescent dye, in this case Fluo-4 (Invitrogen, Carlsbad, Calif.). In the case of partial agonist or agonist ligands, addition of compound to the cells leads to the increase in intracellular Ca$^{+2}$ which is detected by FLIPR (Fluorescence Imaging Plate Reader; Molecular Devices, Sunnyvale, Calif.) technology. In a similar manner, compounds that are antagonists or inverse agonists, block the increase in fluorescence induced by the full histamine H$_4$ agonist histamine, and partial agonists reduce the amount of fluorescence induced by the full histamine H$_4$ agonist histamine. The fluorescence intensities measured before addition of the test compound are subtracted from the fluorescence intensities at later time points. Peak response values determined at each concentration of ligand are expressed as a percentage of the response obtained with the full agonist histamine. Concentration versus response data are analyzed to obtain compound potency as K$_b$ values for antagonists and inverse agonists and as EC$_{50}$ values for partial agonists.

TABLE 2

Potency of compounds in an in vitro assay of histamine H$_4$ activity using FLIPR-Ca$^{+2}$ flux

| Example # | Potency (nM) |
| --- | --- |
| 1 | 4.7 |
| 2 | 5.9 |
| 3 | 5.9 |
| 4 | 4.5 |
| 5 | 16 |
| 6 | 25 |
| 7 | 4.1 |
| 8 | 61.7 |
| 9 | 16 |
| 10 | 1260 |
| 11 | 2000 |
| 12 | 6.9 |
| 13 | 3.3 |
| 14 | 1.5 |
| 15 | 3.2 |
| 16 | 1.4 |
| 17 | 1.2 |
| 18 | 4.9 |
| 19 | 1.6 |
| 20 | 1.4 |
| 21 | 8.3 |
| 22 | 3.0 |
| 23 | 3.0 |
| 24 | 91.2 |
| 25 | 24.0 |
| 26 | 60.3 |
| 27 | 89.1 |
| 28 | 21.9 |

Generally, representative compounds of the invention demonstrated potencies in the above FLIPR assay from about 1 nM to about 10000 nM. Preferred compounds of the invention have potencies at histamine-H$_4$ receptors from about 1 nM to about 2000 nM. More preferred compounds of the invention have potencies at histamine H$_4$ receptors from about 1 nM to about 90 nM.

The potency of compounds of the invention in displacing $^3$H-histamine in competition binding assays is assessed by methods described in Esbenshade, et al., Biochemical Pharmacology (2004), vol. 68, pp. 933-945. In this assay, membranes were prepared from HEK-293 cells transiently transfected with the pCINeo expression vector harboring the histamine H$_4$ receptor by homogenization of the cells on ice in TE buffer (50 mM Tris-HCl buffer, pH 7.4, containing 5 mM EDTA), 1 mM benzamidine, 2 μg/mL aprotinin, 1 μg/mL leupeptin, and 1 μg/mL pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer. Competition radioligand binding assays were performed with increasing concentrations of test compound in the presence of [$^3$H]-histamine incubated at 25° C. for 1 hour in a total volume of 0.5 mL of 50 mM Tris, 5 mM EDTA, pH 7.4. All binding reactions were terminated by filtration under vacuum onto polyethylenimine (0.3%) presoaked Unifilters (PerkinElmer Life Sciences) or Whatman GF/B filters (Whatman, Clifton, N.J.) followed by three brief washes with 4 mL of ice-cold TE buffer. Bound radiolabel was determined by liquid scintillation counting. For all of the radioligand competition binding assays, $IC_{50}$ values and Hill slopes were determined by Hill transformation of the data and $K_i$ values were determined by the Cheng-Prusoff equation. The following table of representative histamine $H_4$ receptor ligands is provided, along with potency values:

| Example # | Binding assay Potency (Ki, nM) |
|---|---|
| 1 | 5.8 |
| 2 | 3.3 |
| 3 | 16.6 |
| 4 | 3 |
| 7 | 12.6 |
| 12 | 2 |
| 13 | 1.8 |
| 14 | 0.9 |
| 15 | 1 |
| 16 | 2.6 |
| 18 | 2.6 |
| 25 | 5.6 |
| 28 | 5.5 |

Generally, representative compounds of the invention demonstrate potencies from about 1 nM to about 10000 nM. Preferred compounds of the invention have potencies at histamine-$H_4$ receptors from about 1 nM to about 1000 nM. More preferred compounds of the invention have potencies at histamine $H_4$ receptors from about 1 nM to about 20 nM.

In addition to the utility of in vitro methods for characterizing the potency of compounds at the $H_4$ receptor, there are animal disease models of available which demonstrate the utility of compounds. There are a number of methods to test the activity of compounds in different pain models that are well known to those skilled in the art. A description of the formalin test in rats, as neuropathic pain models in rats, and general descriptions of methods of testing and descriptions of pain models are found in the book 'Drug Discovery and Evaluation, $2^{nd}$ edition (H. Gerhard Vogel, editor; Springer-Verlag, New York, 2002; pp. 702-706).

The usefulness of histamine $H_4$ receptor ligands in treating pain has been demonstrated (U.S. patent application Ser. No. 11/863,925; also (Coruzzi, et al., *Eur. J. Pharmacol.* 2007, 563, 240-244). This invention discloses the novel utility of the compounds of the invention to treat pain, including multiple types of pain, including inflammatory pain, non-inflammatory pain, and neuropathic pain. Neuropathic pain is distinct from other types of pain (e.g. inflammatory pain) in that it can develop in response to previous or ongoing tissue injury, nerve injury, or diabetes, but it persists long after signs of the original injury or damage have disappeared. Neuropathic pain is not currently well treated, and therefore there is a strong need for methods to treat this particular type of pain. The topic of neuropathic pain has been reviewed in the scientific literature, for example, Smith, et al. Drug Development Research (2001) vol. 54(3), pp. 140-153; Collins and Chessell, Expert Opinion on Emerging Drugs (2005) vol. 10(1), pp. 95-108; Vinik and Mehrabyan, Medical Clinics of North America (2004), vol. 88(4), pp. 947-999; Dray, Urban, and Dickenson, Trends in Pharmacological Sciences (1994) vol.15(6) pp. 190-7; Dworkin, Clinical Journal of Pain (2002) vol. 18(6) pp. 343-9. There do exist a number of animal models of neuropathic pain that can be used to assess the ability of the compounds of the invention to treat neuropathic pain, as discussed herein.

Animal models of neuropathic pain are predictive of efficacy of treatment of neuropathic pain in humans. These models can be used to assess the efficacy of compounds of the invention in treating neuropathic pain. Examples of models well known to those skilled in the art include the Chung model (Kim and Chung, Pain (1992) vol. 50 pp. 355-363) and the Bennett model (Bennett and Xie, Pain (1988) vol.30 pp. 87-107).

Determination of Analgesic Effect Against Inflammatory Pain

To assess the effectiveness of representative compounds of the invention against acute model inflammatory pain, animals were tested in an acute model of carrageenan-induced thermal hyperalgesia (see for example, Honore, et al. *Behavioural Brain Research* (2006) vol. 167 pp. 355-364; Porreca, et al. *Journal of Pharmacology and Experimental Therapeutics* (2006) vol. 318 pp. 195-205). Carrageenan was injected into the test paw of the animal, and after 90 minutes, the test drug was administered by intraperitoneal dosing; the effect on thermal hyperalgesia was assessed in a hotbox assay which was done 30 minutes after the intraperitoneal dosing of the test drug, and the MPE (maximal percent effect) reported by comparison to the control paw (not injected with carrageenan), according to 100 times the withdrawal latency of the carrageenan injected paw (in seconds) divided by the withdrawal latency of the control (not injected with carrageenan) paw. At 30 micromole/kg injected intraperitoneally, 4-piperazin-1-yl-5,6,7a,8,9,10,11,11a-octahydro[1]benzofuro[2,3-h]quinazolin-2-amine (compound of Example 1) showed a 48% MPE. At 100 micromole/kg injected intraperitoneally, 4-piperazin-1-yl-5,6,7a,8,9,10,11,11a-octahydro[1]benzofuro[2,3-h]quinazolin-2-amine (compound of Example 1) showed a 68% MPE. At 100 micromole/kg injected intraperitoneally, (−)-(7aS*,11aS*)-4-piperazin-1-yl-5,6,7a,8,9,10,11,11a-octahydro[1]benzofuro[2,3-h]quinazolin-2-amine (compound of Example 3) showed a 47% MPE. At 100 micromole/kg injected intraperitoneally, (+)-(7aR*,11aR*)-4-piperazin-1-yl-5,6,7a,8,9,10,11,11a-octahydro[1]benzofuro[2,3-h]quinazolin-2-amine (compound of Example 4) showed a 63% MPE. Representative compounds are active in this model, with preferred compounds of the invention active in the model at doses of about 100 micromoles/kg of body weight.

Compounds of the invention are histamine $H_4$ receptor ligands that modulate function of the histamine $H_4$ receptor by altering the activity of the receptor. These compounds may be antagonists that block the action of receptor activation induced by histamine $H_4$ receptor agonists such as histamine; they may be histamine $H_4$ receptor inverse agonists that inhibit the basal activity of the receptor and block the action of receptor activation induced by histamine $H_4$ receptor agonists such as histamine, and they may be partial agonists that partially block the action of receptor activation induced by histamine H$_4$ receptor agonists such as histamine and prevent full activation of histamine H$_4$ receptors.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

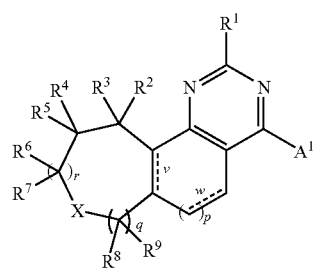

or a pharmaceutically acceptable, salt, ester, or amide thereof, wherein p is 1;
q is 0;
r is 0; and
X is O;
v and w are single or double bonds; with the proviso that w can be a single or a double bond when p is 1;
R$^1$ is selected from hydrogen, —(C═O)—NH-alkylene (NR$^{13}$R$^{14}$), —(C═O)—(NR$^{13}$R$^{14}$), NH$_2$, —NH(acyl), —NH(alkyl), —N(alkyl)$_2$, —NH-alkylene-heteroaryl, —NH-alkylene(NR$^{13}$R$^{14}$), —NH(C═O)-alkylene (NR$^{13}$R$^{14}$), —NH(C═O)aryl, —NR$^{13}$(C═O) NR$^{13}$R$^{14}$, —NHOH, —NHOCH$_3$, —O-alkylene (NR$^{13}$R$^{14}$), alkoxy, alkoxycarbonyl, alkyl, carboxy, cyano, cyanoalkyl, cycloalkyl, fluoroalkyl, fluorocycloalkyl, hydroxyalkyl, and piperazine;
R$^2$, R$^3$, R$^4$, R$^5$, R$^6$, R$^7$, R$^8$ and R$^9$ are each independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkylthio, alkynyl, amido, aryl, carboxy, cyano, cyanoalkyl, cycloalkoxyalkyl, cycloalkyl, cycloalkylalkyl, fluoroalkoxy, fluoroalkyl, fluorocycloalkyl, fluorocycloalkylalkyl, formyl, halogen, heteroaryl, heterocycle, hydrogen, hydroxy, hydroxyalkyl, mercapto, nitro, C(O)NR$^{13}$R$^{14}$, NR$^{11}$COalkyl, —NR$^{13}$R$^{14}$, —N(R$^{13}$)SO$_2$(R$^{14}$), —O-aryl, —O-heteroaryl, —S-aryl, and —SO$_2$ (NR$^{13}$R$^{14}$);
R$^2$ and R$^4$ together with the atom they are attached may form a ring, alternatively, any two of R$^2$, R$^4$, R$^6$, and R$^8$ that are on non-adjacent carbon atoms, may optionally be taken together to form a bridge selected from —CH═CH—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;

R$^{11}$ is selected from alkoxyalkyl, alkyl, cyanoalkyl, cycloalkoxyalkyl, cycloalkyl, cycloalkylalkyl, fluoroalkyl, fluorocycloalkyl, fluorocycloalkylalkyl, hydrogen, and hydroxyalkyl;
R$^{12}$ is selected from the group consisting of alkoxyalkyl, fluoroalkyl, fluorocycloalkyl, fluorocycloalkylalkyl, and hydroxyalkyl;
R$^{13}$ and R$^{14}$ are each independently selected from acyl, alkoxyalkyl, alkoxycarbonyl, alkyl, alkylsulfonyl, amido, aryl, cyanoalkyl, cycloalkoxyalkyl, cycloalkyl, cycloalkylalkyl, fluoroalkyl, fluorocycloalkyl, fluorocycloalkylalkyl, formyl, heteroaryl, heterocycle, hydrogen, hydroxy, and hydroxyalkyl;
A$^1$ is a group of structure A$^2$ or A$^3$
wherein A$^2$ is

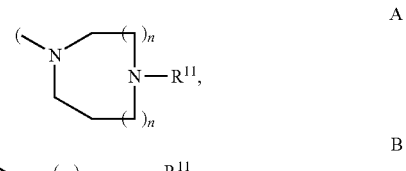

A

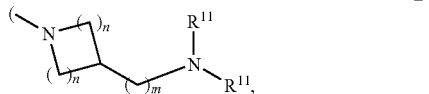

B

C

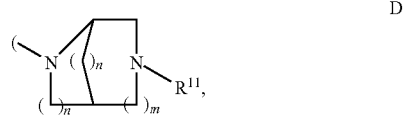

D

E

F

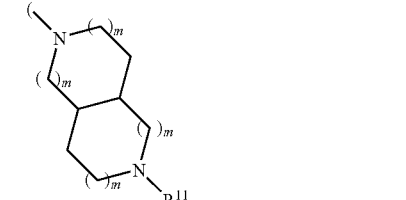

G

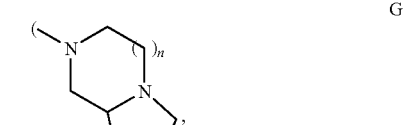

H

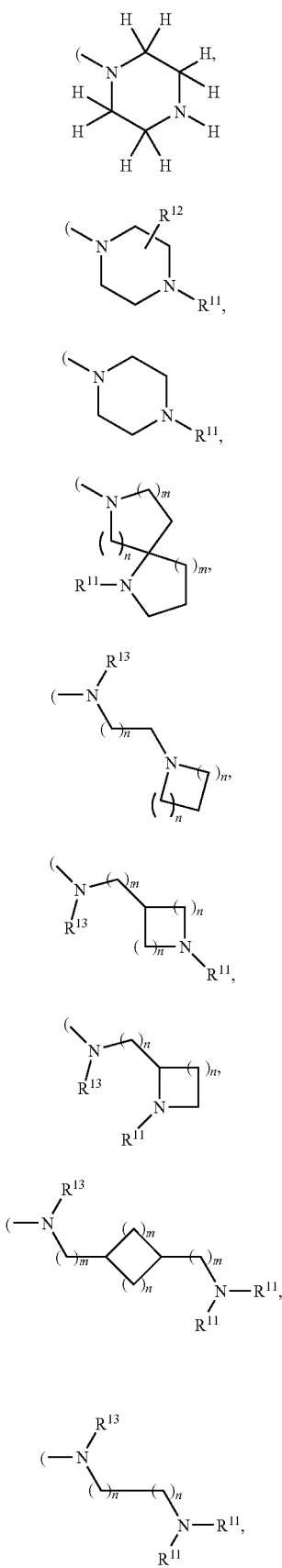
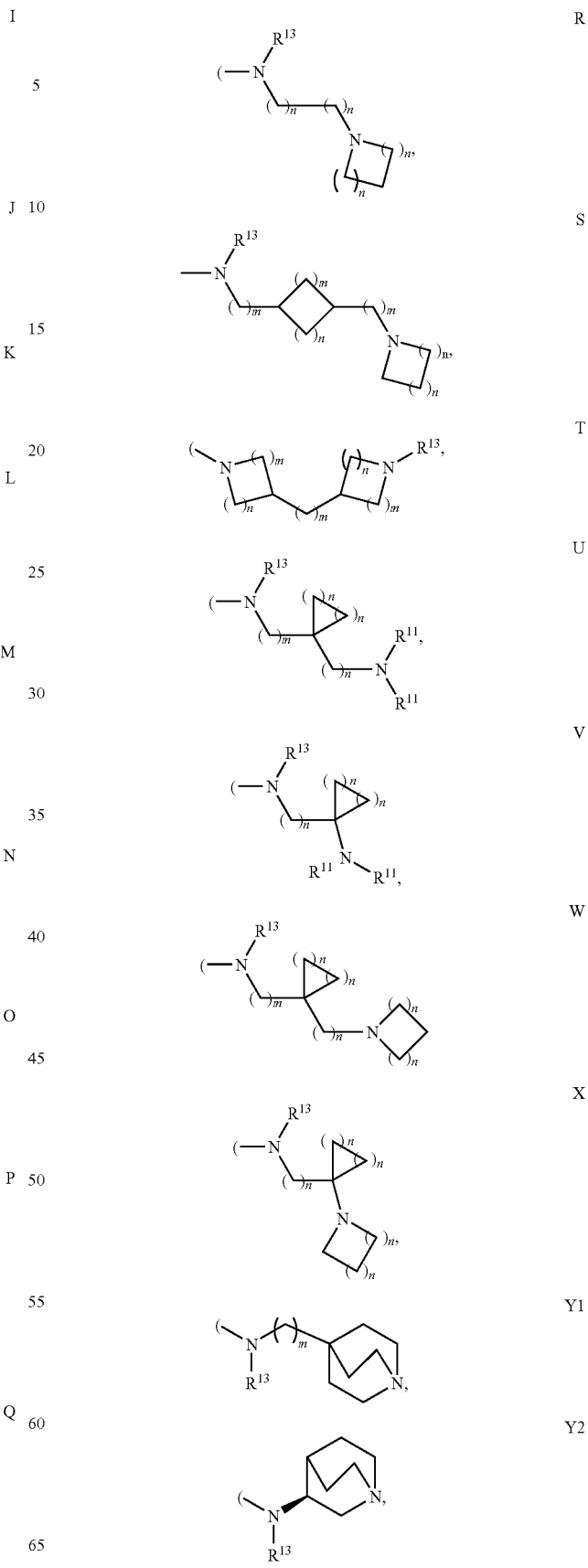

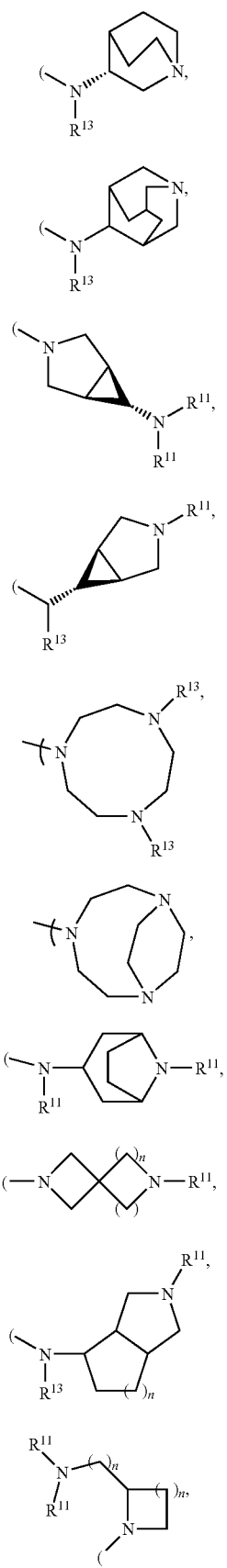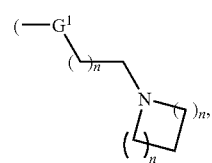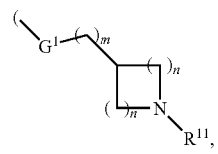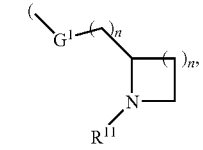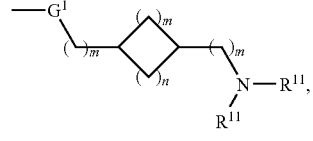
and A³ is selected from
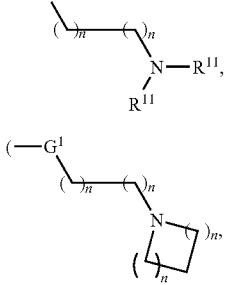

-continued

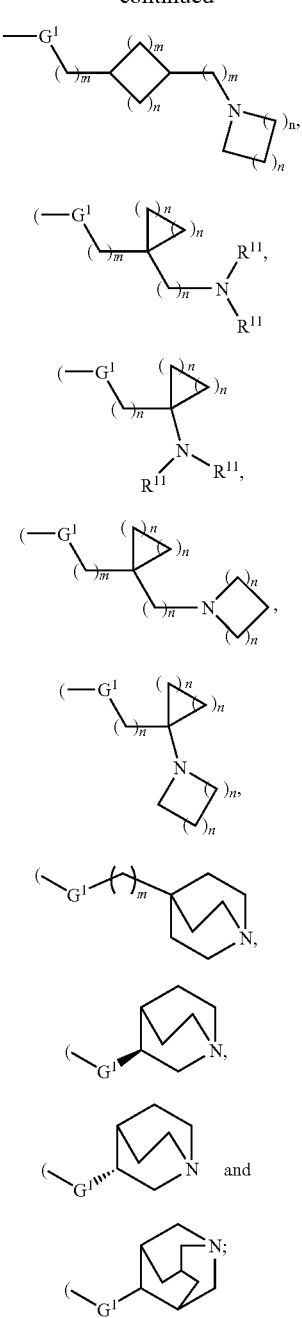

wherein G¹ is O, S, S(O), or S(O)₂;
n is 1, 2, or 3;
m is 0, 1, or 2;
wherein each carbon atom of groups A¹ may be optionally substituted with one or more groups selected from acyl, acyloxy, alkenyl, alkoxy, alkoxyalkoxy, alkoxyalkyl, alkoxycarbonyl, alkyl, alkylsulfonyl, alkylthio, alkynyl, amido, carboxy, cyano, cyanoalkyl, cycloalkoxyalkyl, cycloalkyl, cycloalkylalkyl, fluorine, fluoroalkoxy, fluoroalkyl, fluorocycloalkyl, fluorocycloalkylalkyl, formyl, hydroxy, hydroxyalkyl, mercapto, and nitro.

2. The compound of claim 1, wherein R¹ is selected from hydrogen, NH₂, NHOH, —NHOCH₃, fluoroalkyl, cyanoalkyl, cycloalkyl, fluorocycloalkyl, hydroxyalkyl, cyano, and alkoxy.

3. The compound of claim 1, wherein
v is a double bond;
w is a single bond;
R² and R⁴ form a ring; and
R³ and R⁵ are hydrogen.

4. The compound of claim 3, wherein R¹ is NH₂.

5. The compound of claim 4, wherein A¹ is a group of the formula

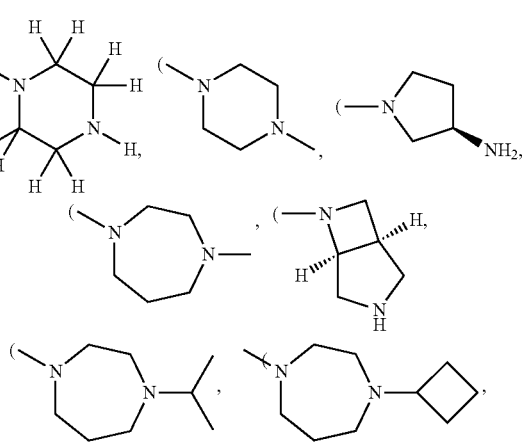

6. The compound of claim 1, wherein
v is a double bond;
w is a double bond;
R² and R⁴ form a ring; and
R³ and R⁵ are hydrogen.

7. The compound of claim 6, wherein R¹ is NH₂.

8. The compound of claim 7, wherein A¹ is a group of the formula

-continued

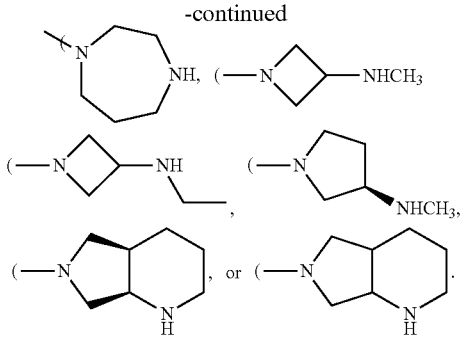

9. The compound of claim 1, wherein the compound is:
4-piperazin-1-yl-5,6,7a,8,9,10,11,11a-octahydro[1]benzofuro[2,3-h]quinazolin-2-amine;
4-[(3R)-3-(methylamino)pyrrolidin-1-yl]-5,6,7a,8,9,10,11,11a-octahydro[1]benzofuro[2,3-h]quinazolin-2-amine;
(7aS,11aS)-4-piperazin-1-yl-5,6,7a,8,9,10,11,11a-octahydro[1]benzofuro[2,3-h]quinazolin-2-amine;
(7aR,11aR)-4-piperazin-1-yl-5,6,7a,8,9,10,11,11a-octahydro[1]benzofuro[2,3-h]quinazolin-2-amine;
4-(4-methyl-1,4-diazepan-1-yl)-5,6,7a,8,9,10,11,11a-octahydro[1]benzofuro[2,3-h]quinazolin-2-amine;
4-(4-methylpiperazin-1-yl)-5,6,7a,8,9,10,11,11a-octahydro[1]benzofuro[2,3-h]quinazolin-2-amine;
4-[(3R)-3-aminopyrrolidin-1-yl]-7a,8,9,10,11,11a-hexahydro[1]benzofuro[2,3-h]quinazolin-2-amine;
4-[(1R,5S)-3,6-diazabicyclo[3.2.0]hept-6-yl]-7a,8,9,10,11,11a-hexahydro[1]benzofuro[2,3-h]quinazolin-2-amine;
4-(1,4-diazepan-1-yl)-5,6,7a,8,9,10,11,11a-octahydro[1]benzofuro[2,3-h]quinazolin-2-amine;
4-(4-isopropyl-1,4-diazepan-1-yl)-5,6,7a, 8,9,10,11,11a-octahydro[1]benzofuro[2,3-h]quinazolin-2-amine; and
4-(4-cyclobutyl-1,4-diazepan-1-yl)-5,6,7a, 8,9,10,11,11a-octahydro[1]benzofuro[2,3-h]quinazolin-2-amine.

10. A pharmaceutical composition comprising a compound of claim 1 and a pharmaceutically acceptable carrier.

* * * * *